(12) United States Patent
Maletinska et al.

(10) Patent No.: US 10,350,271 B2
(45) Date of Patent: Jul. 16, 2019

(54) LIPIDATED PEPTIDES FOR LOWERING BLOOD GLUCOSE

(71) Applicants: USTAV ORGANICKE CHEMIE A BIOCHEMIE AKADEMIE VED CR, V.V.I., Prague (CZ); FYZIOLOGICKY USTAV AKADEMIE VED CR, V.V.I., Prague (CZ)

(72) Inventors: Lenka Maletinska, Prague (CZ); Blanka Zelezna, Prague (CZ); Jaroslav Kunes, Prague (CZ); Veronika Prazienkova, Tabor (CZ)

(73) Assignees: USTAV ORGANICKE CHEMIE A BIOCHEMIE AKADEMIE VED CR, V.V.I., Prague (CZ); FYZIOLOGICKY USTAV AKADEMIE VED CR, V.V.I., Prague (CZ)

( * ) Notice: Subject to any disclaimer, the term of this patent is extended or adjusted under 35 U.S.C. 154(b) by 317 days.

(21) Appl. No.: 15/138,631

(22) Filed: Apr. 26, 2016

(65) Prior Publication Data

US 2016/0228563 A1 Aug. 11, 2016

Related U.S. Application Data

(62) Division of application No. 14/598,160, filed on Jan. 15, 2015, now abandoned.

(60) Provisional application No. 61/927,944, filed on Jan. 15, 2014.

(51) Int. Cl.
| | |
|---|---|
| *A61K 38/22* | (2006.01) |
| *C07K 7/08* | (2006.01) |
| *C07K 14/00* | (2006.01) |
| *C07K 14/575* | (2006.01) |
| *A61K 47/60* | (2017.01) |
| *A61K 47/54* | (2017.01) |
| *A61K 38/00* | (2006.01) |

(52) U.S. Cl.
CPC ............ *A61K 38/22* (2013.01); *A61K 47/542* (2017.08); *A61K 47/60* (2017.08); *C07K 7/08* (2013.01); *C07K 14/001* (2013.01); *C07K 14/575* (2013.01); *A61K 38/00* (2013.01)

(58) Field of Classification Search
CPC ...... A61K 38/00; A61K 47/543; A61K 38/22; C07K 14/47; C07K 14/475
See application file for complete search history.

(56) References Cited

U.S. PATENT DOCUMENTS

| | | | |
|---|---|---|---|
| 9,937,235 B2 * | 4/2018 | Maletinska | A61K 38/2257 |
| 2004/0152769 A1 * | 8/2004 | Ekwuribe | A61K 31/325 |
| | | | 514/478 |

FOREIGN PATENT DOCUMENTS

WO WO2009033668 A2 * 9/2009 ............... A61P 3/00

OTHER PUBLICATIONS

Madsen et al. Structure-activity and protraction relationship of long-acting glucagon-like peptide-1 derivatives: importance of fatty acid length, polarity, and bulkiness. J Med Chem. Nov. 29, 2007;50(24):6126-32. (Year: 2007).*

Lee, Youngsoo, et al., "Distribution of prolactin-releasing peptide mRNA in the rat brain", Elsevier Science Inc., Brain Research Bulletin, vol. 51, No. 2, pp. 171-176, 2000.

\* cited by examiner

*Primary Examiner* — Marcela M Cordero Garcia
*Assistant Examiner* — Jia-Hai Lee
(74) *Attorney, Agent, or Firm* — Notaro, Michaloa & Zaccaria P.C.

(57) ABSTRACT

Lipidated analogs of prolactin-releasing peptides (PrRP) and their use in controlling and lowering blood glucose in mammals is disclosed. Useful compounds included lipidated analogs of PrRP20 and PrRP31. Pharmacological effects are demonstrated both in vitro and in vivo. Peripheral administration of the lipidated peptides towers blood glucose levels. These treatments are applicable for treating impaired glucose tolerance (IGT), and glucose intolerance condition. The disclosed compounds have application in treating medical conditions including diabetes, pre-diabetes, eating disorders, and obesity.

2 Claims, 4 Drawing Sheets

Specification includes a Sequence Listing.

čas [min]

SEQUENCE LISTING

```
<160> NUMBER OF SEQ ID NOS: 99

<210> SEQ ID NO 1
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(24)
<223> OTHER INFORMATION: Xaa is any amino acid, and may encompass 13 or
      24 residues; lipidated in one position by a C8-C18 fatty acid,
      either directly or through a linker
<220> FEATURE:
<221> NAME/KEY: misc_feature
<222> LOCATION: (25)..(25)
<223> OTHER INFORMATION: Xaa is isoleucine, alanine, or phenylglycine
<220> FEATURE:
<221> NAME/KEY: misc_feature
<222> LOCATION: (28)..(28)
<223> OTHER INFORMATION: Xaa is valine or phenylglycine
```

```
<220> FEATURE:
<221> NAME/KEY: misc_feature
<222> LOCATION: (31)..(31)
<223> OTHER INFORMATION: Xaa phenylalanine, tryptophan, pyroglutamic
      acid or an amino acid with a side chain containing CH2-Ar or
      CH2-S-CH2-Ar, wherein Ar represents phenyl or naphtyl, optionally
      substituted by a halogen, methyl or nitro group
<220> FEATURE:
<221> NAME/KEY: misc_feature
<222> LOCATION: (31)..(31)
<223> OTHER INFORMATION: C-term NH2

<400> SEQUENCE: 1

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Arg Pro Xaa Gly Arg Xaa
                20                  25                  30

<210> SEQ ID NO 2
<211> LENGTH: 31
<212> TYPE: PRT
<213> ORGANISM: Artificial Sequence
<220> FEATURE:
<223> OTHER INFORMATION: Synthetic peptide peptide
<220> FEATURE:
<221> NAME/KEY: misc_feature
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (1)..(1)
<223> OTHER INFORMATION: Xaa is serine, threonine or diaminopropionic
      acid
<220> FEATURE:
<221> NAME/KEY: misc_feature
<222> LOCATION: (3)..(3)
<223> OTHER INFORMATION: Xaa is threonine, alanine or methylalanine
<220> FEATURE:
<221> NAME/KEY: misc_feature
<222> LOCATION: (5)..(5)
<223> OTHER INFORMATION: Xaa is glutamine or arginine
<220> FEATURE:
<221> NAME/KEY: misc_feature
<222> LOCATION: (8)..(8)
<223> OTHER INFORMATION: Xaa is methionine or norleucine
<220> FEATURE:
<221> NAME/KEY: misc_feature
<222> LOCATION: (10)..(10)
<223> OTHER INFORMATION: Xaa is threonine or isoleucine
<220> FEATURE:
<221> NAME/KEY: misc_feature
<222> LOCATION: (21)..(21)
<223> OTHER INFORMATION: Xaa is threonine, alanine or methylalanine
<220> FEATURE:
<221> NAME/KEY: misc_feature
<222> LOCATION: (22)..(22)
<223> OTHER INFORMATION: Xaa is glycine or serine
<220> FEATURE:
<221> NAME/KEY: misc_feature
<222> LOCATION: (24)..(24)
<223> OTHER INFORMATION: Xaa is glycine, alanine, proline, or
      N-methylglycine
<220> FEATURE:
<221> NAME/KEY: misc_feature
<222> LOCATION: (25)..(25)
<223> OTHER INFORMATION: Xaa is isoleucine, alanine, or phenylglycine
<220> FEATURE:
<221> NAME/KEY: misc_feature
<222> LOCATION: (28)..(28)
<223> OTHER INFORMATION: Xaa is valine or phenylglycine
<220> FEATURE:
<221> NAME/KEY: misc_feature
<222> LOCATION: (31)..(31)
<223> OTHER INFORMATION: Xaa is phenylalanine, tryptophan, pyroglutamic
``` acid, or an amino acid with a side chain containing CH2-Ar or
CH2-S-CH2-Ar, where Ar represents phenyl or naphtyl, optionally
substituted by halogen, methyl, or nitro group
<220> FEATURE:
<221> NAME/KEY: misc_feature
<222> LOCATION: (31)..(31)
<223> OTHER INFORMATION: C-term NH2

<400> SEQUENCE: 2

Xaa Arg Xaa His Xaa His Ser Xaa Glu Xaa Arg Thr Pro Asp Ile Asn
1               5                   10                  15

Pro Ala Trp Tyr Xaa Xaa Arg Xaa Xaa Arg Pro Xaa Gly Arg Xaa
            20              25                  30

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (10)..(10)
<223> OTHER INFORMATION: Xaa is threonine, alanine, or methylalanine
<220> FEATURE:
<221> NAME/KEY: misc_feature
<222> LOCATION: (11)..(11)
<223> OTHER INFORMATION: Xaa is glycine or serine
<220> FEATURE:
<221> NAME/KEY: misc_feature
<222> LOCATION: (13)..(13)
<223> OTHER INFORMATION: Xaa is glycine, alanine, proline, or
      N-methylglycine
<220> FEATURE:
<221> NAME/KEY: misc_feature
<222> LOCATION: (14)..(14)
<223> OTHER INFORMATION: Xaa is isoleucine, alanine, or phenylglycine
<220> FEATURE:
<221> NAME/KEY: misc_feature
<222> LOCATION: (17)..(17)
<223> OTHER INFORMATION: Xaa is valine or phenylglycine
<220> FEATURE:
<221> NAME/KEY: misc_feature
<222> LOCATION: (20)..(20)
<223> OTHER INFORMATION: Xaa is phenylalanine, tryptophan, pyroglutamic
      acid, or an amino acid with a side chain containing CH2-Ar or
      CH2-S-CH2-Ar, where Ar represents phenyl or naphtyl, optionally
      substituted by halogen, methyl or nitro group
<220> FEATURE:
<221> NAME/KEY: misc_feature
<222> LOCATION: (20)..(20)
<223> OTHER INFORMATION: C-term NH2

<400> SEQUENCE: 3

Thr Pro Asp Ile Asn Pro Ala Trp Tyr Xaa Xaa Arg Xaa Xaa Arg Pro
1               5                   10                  15

Xaa Gly Arg Xaa
            20

<210> SEQ ID NO 4
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature

```
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (3)..(3)
<223> OTHER INFORMATION: Xaa is threonine, alanine, or methylalanine
<220> FEATURE:
<221> NAME/KEY: misc_feature
<222> LOCATION: (5)..(5)
<223> OTHER INFORMATION: Xaa is glutamine or arginine
<220> FEATURE:
<221> NAME/KEY: misc_feature
<222> LOCATION: (8)..(8)
<223> OTHER INFORMATION: Xaa is methionine or norleucine
<220> FEATURE:
<221> NAME/KEY: misc_feature
<222> LOCATION: (10)..(10)
<223> OTHER INFORMATION: Xaa is threonine or isoleucine
<220> FEATURE:
<221> NAME/KEY: misc_feature
<222> LOCATION: (21)..(21)
<223> OTHER INFORMATION: Xaa is threonine, alanine, or methylalanine
<220> FEATURE:
<221> NAME/KEY: misc_feature
<222> LOCATION: (22)..(22)
<223> OTHER INFORMATION: Xaa is glycine or serine
<220> FEATURE:
<221> NAME/KEY: misc_feature
<222> LOCATION: (24)..(24)
<223> OTHER INFORMATION: Xaa is glycine, alanine, proline, or
      N-methylglycine
<220> FEATURE:
<221> NAME/KEY: misc_feature
<222> LOCATION: (25)..(25)
<223> OTHER INFORMATION: Xaa is isoleucine, alanine, or phenylglycine
<220> FEATURE:
<221> NAME/KEY: misc_feature
<222> LOCATION: (28)..(28)
<223> OTHER INFORMATION: Xaa is valine or phenylglycine
<220> FEATURE:
<221> NAME/KEY: misc_feature
<222> LOCATION: (31)..(31)
<223> OTHER INFORMATION: Xaa is phenylalanine, tryptophan, pyroglutamic
      acid, or an amino acid with a side chain containing CH2-Ar or
      CH2-S-CH2-Ar, where Ar represents phenyl or naphtyl, optionally
      substituted by halogen, methyl or nitro group
<220> FEATURE:
<221> NAME/KEY: misc_feature
<222> LOCATION: (31)..(31)
<223> OTHER INFORMATION: C-term NH2

<400> SEQUENCE: 4

Ser Arg Xaa His Xaa His Ser Xaa Glu Xaa Arg Thr Pro Asp Ile Asn
1               5                   10                  15

Pro Ala Trp Tyr Xaa Xaa Arg Xaa Xaa Arg Pro Xaa Gly Arg Xaa
            20                  25                  30

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (10)..(10)
<223> OTHER INFORMATION: Xaa is threonine, alanine, or methylalanine
<220> FEATURE:
```

```
<221> NAME/KEY: misc_feature
<222> LOCATION: (11)..(11)
<223> OTHER INFORMATION: Xaa is glycine or serine
<220> FEATURE:
<221> NAME/KEY: misc_feature
<222> LOCATION: (14)..(14)
<223> OTHER INFORMATION: Xaa is isoleucine, alanine, or phenylglycine
<220> FEATURE:
<221> NAME/KEY: misc_feature
<222> LOCATION: (17)..(17)
<223> OTHER INFORMATION: Xaa is valine or phenylglycine
<220> FEATURE:
<221> NAME/KEY: misc_feature
<222> LOCATION: (20)..(20)
<223> OTHER INFORMATION: C-term NH2

<400> SEQUENCE: 5

Thr Pro Asp Ile Asn Pro Ala Trp Tyr Xaa Xaa Arg Gly Xaa Arg Pro
1               5                   10                  15

Xaa Gly Arg Phe
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (10)..(10)
<223> OTHER INFORMATION: Xaa is threonine, alanine, or methylalanine
<220> FEATURE:
<221> NAME/KEY: misc_feature
<222> LOCATION: (11)..(11)
<223> OTHER INFORMATION: Xaa is glycine or serine
<220> FEATURE:
<221> NAME/KEY: misc_feature
<222> LOCATION: (14)..(14)
<223> OTHER INFORMATION: Xaa is isoleucine, alanine, or phenylglycine
<220> FEATURE:
<221> NAME/KEY: misc_feature
<222> LOCATION: (17)..(17)
<223> OTHER INFORMATION: Xaa is valine or phenylglycine
<220> FEATURE:
<221> NAME/KEY: misc_feature
<222> LOCATION: (20)..(20)
<223> OTHER INFORMATION: Xaa is 1-Nal (naphtylalanine)
<220> FEATURE:
<221> NAME/KEY: misc_feature
<222> LOCATION: (20)..(20)
<223> OTHER INFORMATION: C-term NH2

<400> SEQUENCE: 6

Thr Pro Asp Ile Asn Pro Ala Trp Tyr Xaa Xaa Arg Gly Xaa Arg Pro
1               5                   10                  15

Xaa Gly Arg Xaa
            20

<210> SEQ ID NO 7
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
```

```
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (2)..(2)
<223> OTHER INFORMATION: Xaa is threonine, alanine, or methylalanine
<220> FEATURE:
<221> NAME/KEY: misc_feature
<222> LOCATION: (4)..(4)
<223> OTHER INFORMATION: Xaa is glutamine or arginine
<220> FEATURE:
<221> NAME/KEY: misc_feature
<222> LOCATION: (7)..(7)
<223> OTHER INFORMATION: Xaa is Nle (norleucine)
<220> FEATURE:
<221> NAME/KEY: misc_feature
<222> LOCATION: (20)..(20)
<223> OTHER INFORMATION: Xaa is threonine, alanine, or methylalanine
<220> FEATURE:
<221> NAME/KEY: misc_feature
<222> LOCATION: (21)..(21)
<223> OTHER INFORMATION: Xaa is glycine or serine
<220> FEATURE:
<221> NAME/KEY: misc_feature
<222> LOCATION: (24)..(24)
<223> OTHER INFORMATION: Xaa is isoleucine, alanine, or phenylglycine
<220> FEATURE:
<221> NAME/KEY: misc_feature
<222> LOCATION: (27)..(27)
<223> OTHER INFORMATION: Xaa is valine or phenylglycine
<220> FEATURE:
<221> NAME/KEY: misc_feature
<222> LOCATION: (30)..(30)
<223> OTHER INFORMATION: Xaa is 1-Nal (naphtylalanine)
<220> FEATURE:
<221> NAME/KEY: misc_feature
<222> LOCATION: (30)..(30)
<223> OTHER INFORMATION: C-term NH2

<400> SEQUENCE: 7

Arg Xaa His Xaa His Ser Xaa Glu Thr Arg Thr Pro Asp Ile Asn Pro
1               5                   10                  15

Ala Trp Tyr Xaa Xaa Arg Gly Xaa Arg Pro Xaa Gly Arg Xaa
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (31)..(31)
<223> OTHER INFORMATION: C-term NH2

<400> SEQUENCE: 8

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 9
<211> LENGTH: 31
<212> TYPE: PRT
```

-continued

```
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (31)..(31)
<223> OTHER INFORMATION: C-term NH2

<400> SEQUENCE: 9

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (20)..(20)
<223> OTHER INFORMATION: C-term NH2

<400> SEQUENCE: 10

Thr Pro Asp Ile Asn Pro Ala Trp Tyr Ala Ser Arg Gly Ile Arg Pro
1               5                   10                  15

Val Gly Arg Phe
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: C8-C18 fatty acid bound by an amide bond to an
      amino group of a N-terminal amino acid, either directly or through
      a linker
<220> FEATURE:
<221> NAME/KEY: misc_feature
<222> LOCATION: (10)..(10)
<223> OTHER INFORMATION: Xaa is Threonine or Alanine
<220> FEATURE:
<221> NAME/KEY: misc_feature
<222> LOCATION: (11)..(11)
<223> OTHER INFORMATION: Xaa is Glycine or Serine
<220> FEATURE:
<221> NAME/KEY: misc_feature
<222> LOCATION: (20)..(20)
<223> OTHER INFORMATION: C-term NH2

<400> SEQUENCE: 11

Thr Pro Asp Ile Asn Pro Ala Trp Tyr Xaa Xaa Arg Gly Ile Arg Pro
1               5                   10                  15
```

Val Gly Arg Phe
        20

<210> SEQ ID NO 12
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: palmitic acid
<220> FEATURE:
<221> NAME/KEY: misc_feature
<222> LOCATION: (31)..(31)
<223> OTHER INFORMATION: C-term NH2

<400> SEQUENCE: 12

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: palmitic acid
<220> FEATURE:
<221> NAME/KEY: misc_feature
<222> LOCATION: (20)..(20)
<223> OTHER INFORMATION: C-term NH2

<400> SEQUENCE: 13

Thr Pro Asp Ile Asn Pro Lys Trp Tyr Ala Ser Arg Gly Ile Arg Pro
1               5                   10                  15

Val Gly Arg Phe
        20

<210> SEQ ID NO 14
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: palmitic acid linked to either y-glutamic acid
      or polyoxyethylen
<220> FEATURE:
<221> NAME/KEY: misc_feature
<222> LOCATION: (31)..(31)
<223> OTHER INFORMATION: C-term NH2

<400> SEQUENCE: 14

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 15
<211> LENGTH: 20

-continued

```
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: palmitic acid linked to either y-glutamic acid
      or polyoxyethylen
<220> FEATURE:
<221> NAME/KEY: MOD_RES
<222> LOCATION: (20)..(20)
<223> OTHER INFORMATION: C-term NH2

<400> SEQUENCE: 15

Thr Pro Asp Ile Asn Pro Lys Trp Tyr Ala Ser Arg Gly Ile Arg Pro
1               5                   10                  15

Val Gly Arg Phe
            20

<210> SEQ ID NO 16
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid or myristic acid
<220> FEATURE:
<221> NAME/KEY: misc_feature
<222> LOCATION: (31)..(31)
<223> OTHER INFORMATION: C-term NH2

<400> SEQUENCE: 16

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 17
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid or myristic acid
<220> FEATURE:
<221> NAME/KEY: misc_feature
<222> LOCATION: (31)..(31)
<223> OTHER INFORMATION: C-term NH2

<400> SEQUENCE: 17

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 18
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
```

```
<222> LOCATION: (1)..(1)
<223> OTHER INFORMATION: N-palm
<220> FEATURE:
<221> NAME/KEY: misc_feature
<222> LOCATION: (31)..(31)
<223> OTHER INFORMATION: C-term NH2

<400> SEQUENCE: 18

Ser Arg Thr His Arg His Ser Met Glu Ile Arg Thr Pro Asp Ile Asn
1               5                   10                  15
Pro Ala Trp Tyr Ala Ser Arg Gly Ile Arg Pro Val Gly Arg Phe
            20                  25                  30

<210> SEQ ID NO 19
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (31)..(31)
<223> OTHER INFORMATION: C-term NH2

<400> SEQUENCE: 19

Ser Arg Thr His Arg His Ser Met Glu Ile Arg Thr Pro Asp Ile Asn
1               5                   10                  15
Pro Ala Trp Tyr Ala Ser Arg Gly Ile Arg Pro Val Gly Arg Phe
            20                  25                  30

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (20)..(20)
<223> OTHER INFORMATION: C-term NH2

<400> SEQUENCE: 20

Thr Pro Asp Ile Asn Pro Ala Trp Tyr Thr Gly Arg Gly Ile Arg Pro
1               5                   10                  15
Val Gly Arg Phe
            20

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (20)..(20)
<223> OTHER INFORMATION: C-term NH2
```

```
<400> SEQUENCE: 21

Thr Pro Asp Ile Asn Pro Ala Trp Tyr Ala Ser Arg Gly Ile Arg Pro
1               5                   10                  15

Val Gly Arg Phe
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-oct
<220> FEATURE:
<221> NAME/KEY: misc_feature
<222> LOCATION: (20)..(20)
<223> OTHER INFORMATION: C-term NH2

<400> SEQUENCE: 22

Thr Pro Asp Ile Asn Pro Ala Trp Tyr Ala Ser Arg Gly Ile Arg Pro
1               5                   10                  15

Val Gly Arg Phe
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-dec
<220> FEATURE:
<221> NAME/KEY: misc_feature
<222> LOCATION: (20)..(20)
<223> OTHER INFORMATION: C-term NH2

<400> SEQUENCE: 23

Thr Pro Asp Ile Asn Pro Ala Trp Tyr Ala Ser Arg Gly Ile Arg Pro
1               5                   10                  15

Val Gly Arg Phe
            20

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-dodec
<220> FEATURE:
<221> NAME/KEY: misc_feature
<222> LOCATION: (20)..(20)
<223> OTHER INFORMATION: C-term NH2

<400> SEQUENCE: 24

Thr Pro Asp Ile Asn Pro Ala Trp Tyr Ala Ser Arg Gly Ile Arg Pro
1               5                   10                  15

Val Gly Arg Phe
            20
```

<210> SEQ ID NO 25
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid, myristic acid or stearic acid
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 25

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid or myristic acid
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is 1-Nal
<220> FEATURE:
<221> NAME/KEY: misc_feature
<222> LOCATION: (31)..(31)
<223> OTHER INFORMATION: C-term NH2

<400> SEQUENCE: 26

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid or myristic acid
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)

<223> OTHER INFORMATION: Xaa is PheCl2
<220> FEATURE:
<221> NAME/KEY: misc_feature
<222> LOCATION: (31)..(31)
<223> OTHER INFORMATION: C-term NH2

<400> SEQUENCE: 27

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid or myristic acid
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheNO2
<220> FEATURE:
<221> NAME/KEY: misc_feature
<222> LOCATION: (31)..(31)
<223> OTHER INFORMATION: C-term NH2

<400> SEQUENCE: 28

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid or myristic acid
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheF5
<220> FEATURE:
<221> NAME/KEY: misc_feature
<222> LOCATION: (31)..(31)
<223> OTHER INFORMATION: C-term NH2

<400> SEQUENCE: 29

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

-continued

```
<210> SEQ ID NO 30
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid or myristic acid
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 30

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Tyr
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: palmitic acid or myristic acid
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 31

Ser Arg Ala His Arg His Ser Xaa Glu Ile Arg Thr Pro Asp Ile Asn
1               5                   10                  15

Pro Ala Trp Tyr Ala Ser Arg Gly Ile Arg Pro Val Gly Arg Tyr
            20                  25                  30

<210> SEQ ID NO 32
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (1)..(1)
<223> OTHER INFORMATION: Xaa is Nle
<220> FEATURE:
<221> NAME/KEY: misc_feature
<222> LOCATION: (24)..(24)
<223> OTHER INFORMATION: C-term NH2

<400> SEQUENCE: 32

Xaa Glu Thr Arg Thr Pro Asp Ile Asn Pro Ala Trp Tyr Thr Gly Arg
1               5                   10                  15
```

Gly Ile Arg Pro Val Gly Arg Phe
            20

<210> SEQ ID NO 33
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (27)..(27)
<223> OTHER INFORMATION: C-term NH2

<400> SEQUENCE: 33

Gln His Ser Met Glu Thr Arg Thr Pro Asp Ile Asn Pro Ala Trp Tyr
1               5                   10                  15

Thr Gly Arg Gly Ile Arg Pro Val Gly Arg Phe
            20                  25

<210> SEQ ID NO 34
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (27)..(27)
<223> OTHER INFORMATION: C-term NH2

<400> SEQUENCE: 34

Gln His Ser Met Glu Thr Arg Thr Pro Asp Ile Asn Pro Ala Trp Tyr
1               5                   10                  15

Ala Ser Arg Gly Ile Arg Pro Val Gly Arg Phe
            20                  25

<210> SEQ ID NO 35
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is serine, threonine or diaminopropionic
      acid
<220> FEATURE:
<221> NAME/KEY: misc_feature
<222> LOCATION: (3)..(3)
<223> OTHER INFORMATION: Xaa is threonine, alanine or methylalanine
<220> FEATURE:
<221> NAME/KEY: misc_feature
<222> LOCATION: (5)..(5)
<223> OTHER INFORMATION: Xaa is glutamine or arginine
<220> FEATURE:
<221> NAME/KEY: misc_feature
<222> LOCATION: (8)..(8)
<223> OTHER INFORMATION: Xaa is methionine or norleucine
<220> FEATURE:
<221> NAME/KEY: misc_feature
<222> LOCATION: (10)..(10)

```
<223> OTHER INFORMATION: Xaa is threonine or isoleucine
<220> FEATURE:
<221> NAME/KEY: misc_feature
<222> LOCATION: (21)..(21)
<223> OTHER INFORMATION: Xaa is threonine, alanine or methylalanine
<220> FEATURE:
<221> NAME/KEY: misc_feature
<222> LOCATION: (22)..(22)
<223> OTHER INFORMATION: Xaa is glycine or serine
<220> FEATURE:
<221> NAME/KEY: misc_feature
<222> LOCATION: (24)..(24)
<223> OTHER INFORMATION: Xaa is glycine, alanine, proline, or
      N-methylglycine

<400> SEQUENCE: 35

Xaa Arg Xaa His Xaa His Ser Xaa Glu Xaa Arg Thr Pro Asp Ile Asn
1               5                   10                  15

Pro Ala Trp Tyr Xaa Xaa Arg Xaa
            20

<210> SEQ ID NO 36
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (7)..(7)
<223> OTHER INFORMATION: C-term NH2

<400> SEQUENCE: 36

Ile Arg Pro Val Gly Arg Phe
1               5

<210> SEQ ID NO 37
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(20)
<223> OTHER INFORMATION: C-term NH2

<400> SEQUENCE: 37

Thr Pro Asp Ile Asn Pro Ala Trp Tyr Thr Gly Arg Gly Ile Arg Pro
1               5                   10                  15

Val Gly Arg Phe
            20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(20)
<223> OTHER INFORMATION: C-term NH2

<400> SEQUENCE: 38

Thr Pro Asp Ile Asn Pro Ala Trp Tyr Ala Ser Arg Gly Ile Arg Pro
1               5                   10                  15

Val Gly Arg Phe
            20
```

<210> SEQ ID NO 39
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (31)..(31)
<223> OTHER INFORMATION: C-term NH2

<400> SEQUENCE: 39

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 40
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (31)..(31)
<223> OTHER INFORMATION: C-term NH2

<400> SEQUENCE: 40

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: myr
<220> FEATURE:
<221> NAME/KEY: misc_feature
<222> LOCATION: (20)..(20)
<223> OTHER INFORMATION: C-term NH2

<400> SEQUENCE: 41

Thr Pro Asp Ile Asn Pro Ala Trp Tyr Thr Gly Arg Gly Ile Arg Pro
1               5                   10                  15

Val Gly Arg Phe
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: myr
<220> FEATURE:
<221> NAME/KEY: misc_feature
<222> LOCATION: (20)..(20)

<223> OTHER INFORMATION: C-term NH2

<400> SEQUENCE: 42

Thr Pro Asp Ile Asn Pro Ala Trp Tyr Ala Ser Arg Gly Ile Arg Pro
1               5                   10                  15

Val Gly Arg Phe
            20

<210> SEQ ID NO 43
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 43

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 44
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-oct
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 44

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 45
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-dec
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature

```
<222> LOCATION: (31)..(31)
<223> OTHER INFORMATION: C-term NH2

<400> SEQUENCE: 45

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 46
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-dodec
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 46

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 47
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 47

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 48
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
```

```
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 48

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 49
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-stear
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 49

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 50
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is 1-Nal
<220> FEATURE:
<221> NAME/KEY: misc_feature
<222> LOCATION: (31)..(31)
<223> OTHER INFORMATION: C-term NH2

<400> SEQUENCE: 50

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 51
<211> LENGTH: 31
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 51

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 52
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is 1-Nal
<220> FEATURE:
<221> NAME/KEY: misc_feature
<222> LOCATION: (31)..(31)
<223> OTHER INFORMATION: C-term NH2

<400> SEQUENCE: 52

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 53
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheCl2
<220> FEATURE:
<221> NAME/KEY: misc_feature
<222> LOCATION: (31)..(31)
<223> OTHER INFORMATION: C-term NH2

<400> SEQUENCE: 53

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
```

<210> SEQ ID NO 54
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheCl2
<220> FEATURE:
<221> NAME/KEY: misc_feature
<222> LOCATION: (31)..(31)
<223> OTHER INFORMATION: C-term NH2

<400> SEQUENCE: 54

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheCl2
<220> FEATURE:
<221> NAME/KEY: misc_feature
<222> LOCATION: (31)..(31)
<223> OTHER INFORMATION: C-term NH2

<400> SEQUENCE: 55

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature

```
<222> LOCATION: (31)..(31)
<223> OTHER INFORMATION: Xaa is PheNO2
<220> FEATURE:
<221> NAME/KEY: misc_feature
<222> LOCATION: (31)..(31)
<223> OTHER INFORMATION: C-term NH2

<400> SEQUENCE: 56

Ser Arg Ala His Gln His Ser Xaa Glu Thr Arg Thr Pro Asp Ile Asn
 1               5                  10                  15

Pro Ala Trp Tyr Thr Gly Arg Gly Ile Arg Pro Val Gly Arg Xaa
             20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheNO2
<220> FEATURE:
<221> NAME/KEY: misc_feature
<222> LOCATION: (31)..(31)
<223> OTHER INFORMATION: C-term NH2

<400> SEQUENCE: 57

Ser Arg Ala His Gln His Ser Xaa Glu Thr Arg Thr Pro Asp Ile Asn
 1               5                  10                  15

Pro Ala Trp Tyr Thr Gly Arg Gly Ile Arg Pro Val Gly Arg Xaa
             20                  25                  30

<210> SEQ ID NO 58
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheNO2
<220> FEATURE:
<221> NAME/KEY: misc_feature
<222> LOCATION: (31)..(31)
<223> OTHER INFORMATION: C-term NH2

<400> SEQUENCE: 58

Ser Arg Ala His Gln His Ser Xaa Glu Thr Arg Thr Pro Asp Ile Asn
 1               5                  10                  15

Pro Ala Trp Tyr Thr Gly Arg Gly Ile Arg Pro Val Gly Arg Xaa
             20                  25                  30
```

<210> SEQ ID NO 59
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (15)..(15)
<223> OTHER INFORMATION: Xaa is Nle

<400> SEQUENCE: 59

Ser His Gln Arg Pro Ala Asp Thr His Trp Tyr Pro Arg Gly Xaa Phe
1               5                   10                  15

Pro Thr Ile Gly Arg Ile Thr Ala Arg Asn Gly Glu Val Ser Arg
            20                  25                  30

<210> SEQ ID NO 60
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (15)..(15)
<223> OTHER INFORMATION: Xaa is Nle

<400> SEQUENCE: 60

Ser His Gln Arg Pro Ala Asp Thr His Trp Tyr Pro Arg Gly Xaa Phe
1               5                   10                  15

Pro Thr Ile Gly Arg Ile Thr Ala Arg Asn Gly Glu Val Ser Arg
            20                  25                  30

<210> SEQ ID NO 61
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheF5
<220> FEATURE:
<221> NAME/KEY: misc_feature
<222> LOCATION: (31)..(31)
<223> OTHER INFORMATION: C-term NH2

<400> SEQUENCE: 61

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 62
<211> LENGTH: 31
<212> TYPE: PRT
<213> ORGANISM: Artificial Sequence
<220> FEATURE:
<223> OTHER INFORMATION: Synthetic peptide

```
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: Xaa is PheF5
<220> FEATURE:
<221> NAME/KEY: misc_feature
<222> LOCATION: (31)..(31)
<223> OTHER INFORMATION: C-term NH2

<400> SEQUENCE: 62

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Xaa
            20                  25                  30

<210> SEQ ID NO 63
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 63

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Tyr
            20                  25                  30

<210> SEQ ID NO 64
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (8)..(8)
<223> OTHER INFORMATION: Xaa is Nle
<220> FEATURE:
<221> NAME/KEY: misc_feature
<222> LOCATION: (31)..(31)
<223> OTHER INFORMATION: C-term NH2

<400> SEQUENCE: 64

Ser Arg Ala His Gln His Ser Xaa Glu Thr Arg Thr Pro Asp Ile Asn
1               5                   10                  15

Pro Ala Trp Tyr Thr Gly Arg Gly Ile Arg Pro Val Gly Arg Tyr
            20                  25                  30

<210> SEQ ID NO 65
```

```
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is D-phenylalanine
<220> FEATURE:
<221> NAME/KEY: misc_feature
<222> LOCATION: (2)..(2)
<223> OTHER INFORMATION: Xaa is D-arginine
<220> FEATURE:
<221> NAME/KEY: misc_feature
<222> LOCATION: (20)..(20)
<223> OTHER INFORMATION: C-term NH2

<400> SEQUENCE: 65

Xaa Xaa Gly Val Pro Arg Ile Gly Arg Gly Thr Tyr Trp Ala Pro Asn
1               5                   10                  15

Ile Asp Pro Thr
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: MOD_RES
<222> LOCATION: (1)..(1)
<223> OTHER INFORMATION: Xaa is D-phenylalanine
<220> FEATURE:
<221> NAME/KEY: MOD_RES
<222> LOCATION: (2)..(2)
<223> OTHER INFORMATION: Xaa is D-arginine
<220> FEATURE:
<221> NAME/KEY: misc_feature
<222> LOCATION: (20)..(20)
<223> OTHER INFORMATION: C-term NH2

<400> SEQUENCE: 66

Xaa Xaa Gly Val Pro Arg Ile Gly Arg Gly Thr Tyr Trp Ala Pro Asn
1               5                   10                  15

Ile Asp Pro Thr
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (13)..(13)
<223> OTHER INFORMATION: Xaa is Sar
<220> FEATURE:
<221> NAME/KEY: misc_feature
<222> LOCATION: (20)..(20)
<223> OTHER INFORMATION: C-term NH2

<400> SEQUENCE: 67

Thr Pro Asp Ile Asn Pro Ala Trp Tyr Thr Gly Arg Xaa Ile Arg Pro
1               5                   10                  15
```

Val Gly Arg Phe
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (13)..(13)
<223> OTHER INFORMATION: Xaa is Sar
<220> FEATURE:
<221> NAME/KEY: misc_feature
<222> LOCATION: (20)..(20)
<223> OTHER INFORMATION: C-term NH2

<400> SEQUENCE: 68

Thr Pro Asp Ile Asn Pro Ala Trp Tyr Thr Gly Arg Xaa Ile Arg Pro
1               5                   10                  15

Val Gly Arg Phe
            20

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (10)..(10)
<223> OTHER INFORMATION: Xaa is N-Me-Ala
<220> FEATURE:
<221> NAME/KEY: misc_feature
<222> LOCATION: (20)..(20)
<223> OTHER INFORMATION: C-term NH2

<400> SEQUENCE: 69

Thr Pro Asp Ile Asn Pro Ala Trp Tyr Xaa Ser Arg Gly Ile Arg Pro
1               5                   10                  15

Val Gly Arg Phe
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (10)..(10)
<223> OTHER INFORMATION: Xaa is N-Me-Ala
<220> FEATURE:
<221> NAME/KEY: misc_feature
<222> LOCATION: (20)..(20)
<223> OTHER INFORMATION: C-term NH2

<400> SEQUENCE: 70

Thr Pro Asp Ile Asn Pro Ala Trp Tyr Xaa Ser Arg Gly Ile Arg Pro
1               5                   10                  15

Val Gly Arg Phe
          20

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(20)
<223> OTHER INFORMATION: C-term NH2

<400> SEQUENCE: 71

Thr Pro Asp Ile Asn Pro Ala Trp Tyr Thr Gly Arg Gly Ala Arg Pro
1               5                   10                  15

Phe Gly Arg Phe
          20

<210> SEQ ID NO 72
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (20)..(20)
<223> OTHER INFORMATION: C-term NH2

<400> SEQUENCE: 72

Thr Pro Asp Ile Asn Pro Ala Trp Tyr Thr Gly Arg Gly Ala Arg Pro
1               5                   10                  15

Phe Gly Arg Phe
          20

<210> SEQ ID NO 73
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (20)..(20)
<223> OTHER INFORMATION: C-term NH2

<400> SEQUENCE: 73

Thr Pro Asp Ile Asn Pro Ala Trp Tyr Ala Ser Arg Pro Phe Arg Pro
1               5                   10                  15

Val Gly Arg Phe
          20

<210> SEQ ID NO 74
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr

```
<220> FEATURE:
<221> NAME/KEY: misc_feature
<222> LOCATION: (20)..(20)
<223> OTHER INFORMATION: C-term NH2

<400> SEQUENCE: 74

Thr Pro Asp Ile Asn Pro Ala Trp Tyr Ala Ser Arg Pro Phe Arg Pro
1               5                   10                  15

Val Gly Arg Phe
        20

<210> SEQ ID NO 75
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is Nle
<220> FEATURE:
<221> NAME/KEY: misc_feature
<222> LOCATION: (24)..(24)
<223> OTHER INFORMATION: C-term NH2

<400> SEQUENCE: 75

Xaa Glu Thr Arg Thr Pro Asp Ile Asn Pro Ala Trp Tyr Thr Gly Arg
1               5                   10                  15

Gly Ile Arg Pro Val Gly Arg Phe
        20

<210> SEQ ID NO 76
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (1)..(1)
<223> OTHER INFORMATION: Xaa is Nle
<220> FEATURE:
<221> NAME/KEY: misc_feature
<222> LOCATION: (24)..(24)
<223> OTHER INFORMATION: C-term NH2

<400> SEQUENCE: 76

Xaa Glu Thr Arg Thr Pro Asp Ile Asn Pro Ala Trp Tyr Thr Gly Arg
1               5                   10                  15

Gly Ile Arg Pro Val Gly Arg Phe
        20

<210> SEQ ID NO 77
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (27)..(27)
<223> OTHER INFORMATION: C-term NH2

<400> SEQUENCE: 77
```

Gln His Ser Met Glu Thr Arg Thr Pro Asp Ile Asn Pro Ala Trp Tyr
1               5                   10                  15
Thr Gly Arg Gly Ile Arg Pro Val Gly Arg Phe
            20                  25

<210> SEQ ID NO 78
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (27)..(27)
<223> OTHER INFORMATION: C-term NH2

<400> SEQUENCE: 78

Gln His Ser Met Glu Thr Arg Thr Pro Asp Ile Asn Pro Ala Trp Tyr
1               5                   10                  15
Thr Gly Arg Gly Ile Arg Pro Val Gly Arg Phe
            20                  25

<210> SEQ ID NO 79
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-oct
<220> FEATURE:
<221> NAME/KEY: misc_feature
<222> LOCATION: (20)..(20)
<223> OTHER INFORMATION: C-term NH2

<400> SEQUENCE: 79

Thr Pro Asp Ile Asn Pro Ala Trp Tyr Ala Ser Arg Gly Ile Arg Pro
1               5                   10                  15
Val Gly Arg Phe
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-dec
<220> FEATURE:
<221> NAME/KEY: misc_feature
<222> LOCATION: (20)..(20)
<223> OTHER INFORMATION: C-term NH2

<400> SEQUENCE: 80

Thr Pro Asp Ile Asn Pro Ala Trp Tyr Ala Ser Arg Gly Ile Arg Pro
1               5                   10                  15
Val Gly Arg Phe
            20

```
<210> SEQ ID NO 81
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-dodec
<220> FEATURE:
<221> NAME/KEY: misc_feature
<222> LOCATION: (20)..(20)
<223> OTHER INFORMATION: C-term NH2

<400> SEQUENCE: 81

Thr Pro Asp Ile Asn Pro Ala Trp Tyr Ala Ser Arg Gly Ile Arg Pro
1               5                   10                  15

Val Gly Arg Phe
            20

<210> SEQ ID NO 82
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (31)..(31)
<223> OTHER INFORMATION: C-term NH2

<400> SEQUENCE: 82

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 83
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (31)..(31)
<223> OTHER INFORMATION: C-term NH2

<400> SEQUENCE: 83

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 84
<211> LENGTH: 31
<212> TYPE: PRT
<213> ORGANISM: Artificial Sequence
<220> FEATURE:
<223> OTHER INFORMATION: Synthetic peptide
<220> FEATURE:
```

<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (31)..(31)
<223> OTHER INFORMATION: C-term -NHMe

<400> SEQUENCE: 84

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 85
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (31)..(31)
<223> OTHER INFORMATION: C-term -NOMe

<400> SEQUENCE: 85

Ser Arg Thr His Arg His Ser Met Glu Ile Arg Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 86
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-myr
<220> FEATURE:
<221> NAME/KEY: misc_feature
<222> LOCATION: (31)..(31)
<223> OTHER INFORMATION: C-term NH2

<400> SEQUENCE: 86

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 87
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm
<220> FEATURE:
<221> NAME/KEY: misc_feature
<222> LOCATION: (31)..(31)
<223> OTHER INFORMATION: C-term NH2

<400> SEQUENCE: 87

Ser Arg Ala His Gln His Ser Met Glu Thr Arg Thr Pro Asp Ile Asn
1               5                   10                  15

Pro Ala Trp Tyr Thr Gly Arg Gly Ile Arg Pro Val Gly Arg Phe
            20                  25                  30

<210> SEQ ID NO 88
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: N-palm
<220> FEATURE:
<221> NAME/KEY: misc_feature
<222> LOCATION: (31)..(31)
<223> OTHER INFORMATION: C-term NH2

<400> SEQUENCE: 88

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 89
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (5)..(5)
<223> OTHER INFORMATION: N-palm
<220> FEATURE:
<221> NAME/KEY: misc_feature
<222> LOCATION: (20)..(20)
<223> OTHER INFORMATION: C-term NH2

<400> SEQUENCE: 89

Thr Pro Asp Ile Lys Pro Ala Trp Tyr Ala Ser Arg Gly Ile Arg Pro
1               5                   10                  15

Val Gly Arg Phe
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (7)..(7)
<223> OTHER INFORMATION: N-palm
<220> FEATURE:
<221> NAME/KEY: misc_feature
<222> LOCATION: (20)..(20)
<223> OTHER INFORMATION: C-term NH2

<400> SEQUENCE: 90

Thr Pro Asp Ile Asn Pro Lys Trp Tyr Ala Ser Arg Gly Ile Arg Pro
1               5                   10                  15

Val Gly Arg Phe

```
                   20

<210> SEQ ID NO 91
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (18)..(18)
<223> OTHER INFORMATION: N-palm
<220> FEATURE:
<221> NAME/KEY: misc_feature
<222> LOCATION: (31)..(31)
<223> OTHER INFORMATION: C-term NH2

<400> SEQUENCE: 91

Ser Arg Thr His Arg His Ser Met Glu Ile Arg Thr Pro Asp Ile Asn
1               5                   10                  15

Pro Lys Trp Tyr Ala Ser Arg Gly Ile Arg Pro Val Gly Arg Phe
            20                  25                  30

<210> SEQ ID NO 92
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: N-gamma-E(N-palm)
<220> FEATURE:
<221> NAME/KEY: misc_feature
<222> LOCATION: (31)..(31)
<223> OTHER INFORMATION: C-term NH2

<400> SEQUENCE: 92

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 93
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: N-GABA(N-palm)
<220> FEATURE:
<221> NAME/KEY: misc_feature
<222> LOCATION: (31)..(31)
<223> OTHER INFORMATION: C-term NH2

<400> SEQUENCE: 93

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 94
<211> LENGTH: 31
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: (N-palm)gamma-E
<220> FEATURE:
<221> NAME/KEY: misc_feature
<222> LOCATION: (31)..(31)
<223> OTHER INFORMATION: C-term NH2

<400> SEQUENCE: 94

Ser Arg Thr His Arg His Ser Met Glu Ile Arg Thr Pro Asp Ile Asn
1               5                   10                  15
Pro Ala Trp Tyr Ala Ser Arg Gly Ile Arg Pro Val Gly Arg Phe
            20                  25                  30

<210> SEQ ID NO 95
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: N-gamma-E(N-palm)
<220> FEATURE:
<221> NAME/KEY: misc_feature
<222> LOCATION: (31)..(31)
<223> OTHER INFORMATION: C-term NH2

<400> SEQUENCE: 95

Ser Glu Thr His Arg His Ser Met Glu Ile Lys Thr Pro Asp Ile Asn
1               5                   10                  15
Pro Ala Trp Tyr Ala Ser Arg Gly Ile Arg Pro Val Gly Arg Phe
            20                  25                  30

<210> SEQ ID NO 96
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: N-gamma-E(N-palm)
<220> FEATURE:
<221> NAME/KEY: misc_feature
<222> LOCATION: (31)..(31)
<223> OTHER INFORMATION: C-term NH2

<400> SEQUENCE: 96

Ser Glu Thr His Glu His Ser Met Glu Ile Lys Thr Pro Asp Ile Asn
1               5                   10                  15
Pro Ala Trp Tyr Ala Ser Arg Gly Ile Arg Pro Val Gly Arg Phe
            20                  25                  30

<210> SEQ ID NO 97
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: N-palm(N-POE)
<220> FEATURE:
```

```
<221> NAME/KEY: misc_feature
<222> LOCATION: (31)..(31)
<223> OTHER INFORMATION: C-term NH2

<400> SEQUENCE: 97

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 98
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (11)..(11)
<223> OTHER INFORMATION: N-POE(N-palm)
<220> FEATURE:
<221> NAME/KEY: misc_feature
<222> LOCATION: (31)..(31)
<223> OTHER INFORMATION: C-term NH2

<400> SEQUENCE: 98

Ser Glu Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30

<210> SEQ ID NO 99
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: N-palm(N-POE)
<220> FEATURE:
<221> NAME/KEY: MOD_RES
<222> LOCATION: (11)..(11)
<223> OTHER INFORMATION: N-palm(N-POE)
<220> FEATURE:
<221> NAME/KEY: misc_feature
<222> LOCATION: (31)..(31)
<223> OTHER INFORMATION: C-term NH2

<400> SEQUENCE: 99

Ser Arg Thr His Arg His Ser Met Glu Ile Lys Thr Pro Asp Ile Asn
1               5                   10                  15

Pro Ala Trp Tyr Ala Ser Arg Gly Ile Arg Pro Val Gly Arg Phe
            20                  25                  30
```

LIPIDATED PEPTIDES FOR LOWERING BLOOD GLUCOSE

CROSS-REFERENCE

This application claims the benefit of and is a divisional of U.S. application Ser. No. 14/598,160, filed Jan. 15, 2015. U.S. application Ser. No. 14/598,160 is incorporated by reference, including incorporation of all Sequence Listings filed therewith. This application also claims the benefit of U.S. Provisional Application No. 61/927,944 filed Jan. 15, 2014, which is incorporated by reference herein in its entirety.

SEQUENCE LISTING

The instant application contains a Sequence Listing which has been submitted in computer readable text format and also in paper format.

FIELD

The embodiments described herein relate generally to the field of medicine, to metabolism regulation, to prolactin releasing peptides, and in particular to the use of lipidated prolactin-releasing peptides (PrRP) for treating elevated blood glucose levels and related medical conditions.

INCORPORATION BY REFERENCE

All publications, patents, and patent applications mentioned in this specification are herein incorporated by reference to the same extent as if each individual publication, patent, or patent application was specifically and individually indicated to be incorporated by reference, and as if set forth in their entireties.

BACKGROUND 10 to 15 percent of adults in the United States have either impaired glucose tolerance or impaired fasting glucose (Rao S. S. et al., American Family Physician 69 (8), 1961). Impaired glucose tolerance is a pre-diabetic state of hyperglycemia that is associated with insulin resistance and increased risk of cardiovascular pathology, and which may precede type 2 diabetes mellitus (Barr E. L. et al., Circulation 116 (2): 151-7, 2007).

Type 2 diabetes is a complex polygenic disorder currently affecting the lives of over 170 million people worldwide, with that number predicted to double by 2030 [Wild S. et al., Diabetes Care 27:1047-1053, 2004]. It is characterized by insulin resistance, impaired glucose-stimulated insulin release (e.g., pancreatic β-cell dysfunction), and by inappropriate secretion of glucagon, which can be manifested as chronic hyperglycemia.

SUMMARY

Disclosed herein in certain embodiments is a method of treating a subject diagnosed as having or being susceptible to one or more disorders characterized by an increased level of glucose in blood, comprising the step of administering to the subject a lipidated analog of prolactin releasing peptide (PrRP) having the formula:

(Formula 1; SEQ ID NO: 1)
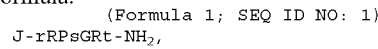

wherein
r is isoleucine, alanine, or phenylglycine;
s is valine or phenylglycine;
t is phenylalanine, tryptophan, pyroglutamic acid or an amino acid with a side chain containing $CH_2$—Ar or $CH_2$—S—$CH_2$—Ar, wherein Ar represents phenyl or naphthyl, optionally substituted by a halogen, methyl or nitro group; and J represents a chain of 13 or 24 amino acids lipidated in one position by X, wherein X=$X^1$ or $X^2X^1$;

wherein $X^1$ is a C8 to C18 fatty acid bound to an amino acid having at least one free amino group, SH group, or OH group, either directly by an amide bond or through $X^2$;

and wherein $X^2$ is a hydrophilic linker selected from the group consisting of a polyoxyethylene moiety, an arylalkyl moiety, and a saturated or unsaturated, linear or branched C3-C8 hydrocarbon chain, wherein one or more carbon atoms may be replaced by heteroatoms selected from the group comprising N, S, and O, said hydrocarbon chain carrying at least one amino group or carboxylic acid group, one of which can be substituted to form
$CONH_2$;
NH-polyoxyethylene;
$COOM^1$; wherein $M^1$ is alkali metal;
CN;
$COOR^1$, $COR^1$, $CONHR^1$; wherein $R^1$ is lower alkyl, aryl alkyl, polyoxyethylene, methylpolyoxyethylene, or aminoethylpolyoxyethylene;
$(CHOH)nR^2$; wherein $R^2$ is H or COOH and n is an integer from 2 to 10; or
$(CH)nN+(R')_3$; wherein each R is independently H or C1-C4 alkyl.

In some embodiments, the method comprises a step of administering to the subject of treatment a lipidated analog of prolactin releasing peptide (PrRP) having the formula:

(Formula 2; SEQ ID NO: 2)
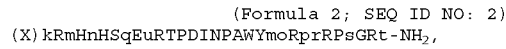

wherein
k is serine, threonine, or diaminopropionic acid;
m is threonine, alanine, or methylalanine;
n is glutamine or arginine;
q is methionine or norleucine;
u is threonine or isoleucine;
o is glycine or serine;
p is glycine, alanine, proline or N-methylglycine;
r is isoleucine, alanine or phenylglycine;
s is valine or phenylglycine; and
t is phenylalanine, tryptophan, pyroglutamic acid, or an amino acid with a side chain containing $CH_2$—Ar or $CH_2$—S—$CH_2$—Ar, where Ar represents phenyl or naphthyl, optionally substituted by a halogen, methyl or nitro group.

In some embodiments, the disorder is characterized by insulin resistance, impaired glucose-stimulated insulin release (e.g., pancreatic β-cell dysfunction) and/or by inappropriate secretion of glucagon. In some embodiments, the disorder is hyperglycemia or diabetes. In some embodiments, the hyperglycemia is a chronic hyperglycemia. In some embodiments, the diabetes is a type 2 diabetes. In some embodiments, the type 2 diabetes is associated with a second disorder. The second disorder can be, e.g., obesity, cardiovascular disease, hypertension or dyslipidemia.

In some embodiments, the method comprises a step of administering to the subject of treatment a lipidated analog of prolactin releasing peptide (PrRP) having the formula (X)kRmHnHSqEuRTPDINPAWYmoRprRPsGRt-$NH_2$ (Formula 2; SEQ ID NO: 2), wherein kRmHnHSqEuRTP-DINPAWYmoRp (SEQ ID NO: 35) is shortened by eliminating 1 to 11 amino acids.

In some embodiments, the method comprises a step of administering to the subject of treatment a lipidated analog of prolactin releasing peptide (PrRP) having the formula (X)kRmHnHSqEuRTPDINPAWYmoRprRPsGRt-NH$_2$ (Formula 2; SEQ ID NO 2), wherein kRmHnHSqEuRTP-DINPAWYmoRp (SEQ ID NO: 35) is shortened by eliminating 1 to 11 amino acids from its N-terminus or its C-terminus.

In some embodiments, the method comprises a step of administering to the subject of treatment a lipidated analog of prolactin releasing peptide (PrRP) having the formula (X)kRmHnHSqEuRTPDINPAWYmoRprRPsGRt-NH$_2$ (Formula 2; SEQ ID NO: 2), wherein kRmHnHSqEuRTP-DINPAWYmoRp (SEQ ID NO: 35) is shortened by eliminating 1 to 11 amino acids from its N-terminus.

In some embodiments, the method comprises a step of administering to the subject of treatment a lipidated analog of prolactin releasing peptide (PrRP) having the formula (X)kRmHnHSqEuRTPDINPAWYmoRprRPsGRt-NH$_2$ (Formula 2; SEQ ID NO: 2), wherein kRmHnHSqEuRTP-DINPAWYmoRp (SEQ NO: 35) is shortened by eliminating 1 to 11 amino acids from its C-terminus.

In some embodiments, the method comprises a step of administering to the subject of treatment a lipidated analog of prolactin releasing peptide (PrRP) having the formula:

```
                              (Formula 2; SEQ ID NO: 2)
(X)kRmHnHSqEuRTPDINPAWYmoRprRPsGRt-NH2,
or
                              (Formula 3; SEQ ID NO: 3)
(X)TPDINPAWYmoRprRPsGRt-NH2,
``` wherein
k is serine, threonine, or diaminopropionic acid;
m is threonine, alanine, or methylalanine;
n is glutamine or arginine;
q is methionine or norleucine;
u is threonine or isoleucine;
o is glycine or serine;
p is glycine, alanine, proline, or N-methylglycine;
r is isoleucine, alanine, or phenylglycine;
s is valine or phenylglycine; and
t is phenylalanine, tryptophan, pyroglutamic acid, or an amino acid with a side chain containing CH$_2$—Ar or CH$_2$—S—CH$_2$—Ar, where Ar represents phenyl or naphthyl, optionally substituted by a halogen, methyl or nitro group, wherein the binding affinity of said lipidated analog of prolactin releasing peptide (PrRP) towards GPR10 receptor expressed in rat hypophyseal cells is not higher than $10^{-6}$ mol·l$^{-1}$.

In some embodiments, the method comprises a step of administering to the subject of treatment a lipidated analog of prolactin releasing peptide (PrRP) having the formula:

```
                              (Formula 4; SEQ ID NO: 4)
(X)SRmHnHSqEuRTPDINPAWYmoRprRPsGRt-NH2,
``` wherein
m is threonine, alanine, or methylalanine;
n is glutamine or arginine;
q is methionine or norleucine;
n is threonine or isoleucine;
o is glycine or serine;
p is glycine, alanine, proline, or N-methylglycine;
r is isoleucine, alanine, or phenylglycine,
s is valine or phenylglycine; and
t is phenylalanine, tryptophan, pyroglutamic acid, or an amino acid with a side chain containing CH$_2$—Ar or CH$_2$—S—CH$_2$—Ar, where Ar represents phenyl or naphthyl, optionally substituted by a halogen, methyl or nitro group; wherein X=X$^1$ or X$^1$X$^2$, and wherein X$^1$ is a C8-C18 fatty acid bound to an amino acid of formula 4, either directly by an amide bond, or through X$^2$.

In some embodiments, the method comprises a step of administering to the subject of treatment a lipidated analog of prolactin releasing peptide (PrRP) having the formula J-rRPsGRt-NH$_2$ (Formula 1; SEQ ID NO: 1); wherein t is selected from the group consisting of histidine, benzylhistidine, naphthylalanine, tryptophan, pyroglutamic acid, benzylcysteine, benzyl-O-glutamate, norleucine, dichlorophenylalanine, tetrachlorophynylalanine pentafluorophenylalanine, methyl-O-phenylalanine, methyl-NH-phenylalanine, and nitrophenylalanine.

In some embodiments, the method comprises a step of administering to the subject of treatment a lipidated analog of prolactin releasing peptide (PrRP) having the formula:

```
                              (Formula 5; SEQ ID NO: 5)
(X)TPDINPAWYmoRGrRPsGRF-NH2;

(Formula 6; SEQ ID NO: 6)
(X)TPDINPAWYmoRGrRPsGR 1-Nal-NH2;
or
                              (Formula 7; SEQ ID NO: 7)
(X)RmHnHSNleETRTPDINPAWYmoRGrRPsGR 1-Nal-NH2;
``` wherein,
1-nal is naphthylalanine;
m is threonine, alanine, or methylalanine;
n is glutamine or arginine;
q is methionine or norleucine;
u is threonine or isoleucine;
o is glycine or serine;
p is glycine, alanine, proline, or N-methylglycine;
s is isoleucine, alanine, or phenylglycine;
s is valine or phenylglycine; and
t is phenylalanine, tryptophan, pyroglutamic acid, or an amino acid with a side chain containing CH2-Ar or CH2-S—CH2-Ar, where Ar represents phenyl or naphthyl, optionally substituted by a halogen, methyl, or nitro group.

In some embodiments, the method comprises a step of administering to the subject of treatment a lipidated analog of prolactin releasing peptide (PrRP) having the formula:

```
                              (Formula 10; SEQ ID NO: 10)
(X)TPDINPAWYASRGIRPVGRF-NH2;
or
                              (Formula 8; SEQ ID NO: 8)
(X)SPTHRHSMEIRTPDINPAWYASRGIRPVGRF-NH2,
``` wherein X=X$^1$ or X$^2$X$^1$, wherein X$^1$ is a C12 to C16 fatty acid bound to an amino acid of formula 10 or formula 8, either directly by an amide bond or through X$^2$, and wherein X$^2$ is selected from the group consisting of β-alanine, γ-amino butyric acid, polyoxyethylene, and γ-glutamic acid.

In some embodiments, the method comprises a step of administering to the subject of treatment a lipidated analog of prolactin releasing peptide (PrRP) having the formula:

```
                              (Formula 10; SEQ ID NO: 10)
(X)TPDINPAWYASRGIRPVGRF-NH2;
or
                              (Formula 8; SEQ ID NO: 8)
(X)SRTHRHSMEIRTPDINPAWYASRGIRPVGRF-NH2,
``` wherein X=$X^1$ or $X^2X^1$, wherein $X^1$ is myristic acid or palmitic acid, and wherein $X^2$ is γ-glutamic acid or polyexyethylene.

In some embodiments, the method comprises a step of administering to the subject of treatment a lipidated analog of prolactin releasing peptide (PrRP) having the formula:

```
                                (Formula 10; SEQ ID NO: 10)
(X) TPDINPAWYASRGIRPVGRF-NH2;
or
                                (Formula 8; SEQ ID NO: 8)
(X) SRTHRHSMEIRTPDINPAWYASRGIRPVGRF-NH2,
``` wherein X=$X^1$ or $X^2X^1$, wherein $X^1$ is myristic acid or palmitic acid, and wherein $X^2$ is γ-glutamic acid or polyexyethylene, and wherein $X^1$ is bound to amino acid 1, 5, or 7 of formula 10, or 1, 11, or 18 of formula 8, either directly or through $X^2$.

In some embodiments, the method comprises a step of administering to the subject of treatment a lipidated analog of prolactin releasing peptide (PrRP) having the formula

```
                                (Formula 10; SEQ ID NO: 10)
(X) TPDINPAWYASRGIRPVGRF-NH2;
or
                                (Formula 8; SEQ ID NO: 8)
(X) SRTHRHSMEIRTPDINPAWYASRGIRPVGRF-NH2,
``` wherein $X^1$ is myristic acid or palmitic acid, and wherein $X^2$ is γ-glutamic acid or polyexyethylene, and wherein $X^1$ is bound to amino acid 1 or 5 of formula 10, or 1 or 11 of formula 8, either directly or through $X^2$.

In some embodiments, the method comprises a step of administering to the subject of treatment a lipidated analog of prolactin releasing peptide (PrRP) selected from the group consisting of:

```
                                     (SEQ ID NO: 12)
SRTHRHSMEIK(palm)TPDINPAWYASRGIRPVGRF-NH2;
                                     (SEQ ID NO: 13)
TPDINPK(palm)WYASRGIRPVGRF-NH2;
                                     (SEQ ID NO: 14)
SRTHRHSMEIKTPDINPAWYASRGIRPVGRF-NH2; and
       |
       X2(palm)
                                     (SEQ ID NO: 15)
TPDINPKWYASRGIRPVGRF-NH2;
       |
       X2(palm)
``` wherein palm is palmitic acid, and wherein $X^2$ is γ-glutamic acid or polyoxyethylene.

In some embodiments, the method comprises a step of administering to the subject of treatment a lipidated analog of of prolactin releasing peptide (PrRP) selected from the group consisting of:

```
                                         (SEQ ID NO: 16)
X1-SRAHQHSMETRTPDINPAWYTGRGIRPVGRF-NH2;
                                         (SEQ ID NO: 17)
X1-SRTHRHSMEIRTPDINPAWYASRGIRPVGRF-NH2;
                                         (SEQ ID NO: 18)
(N-palm)-SRTHRHSMEIRTPDINPAWYASRGIRPVGRF-NHMe;
                                         (SEQ ID NO: 19)
(N-palm)-SRTHRHSMEIRTPDINPAWYASRGIRPVGRF-NOMe;
                                         (SEQ ID NO: 20)
(N-myr)-TPDINPAWYTGRGIRPVGRF-NH2;
                                         (SEQ ID NO: 21)
(N-myr)-TPDINPAWYASRGIRPVGRF-NH2;
                                         (SEQ ID NO: 22)
(N-oct)-TPDINPAWYASRGIRPVGRF-NH2;
                                         (SEQ ID NO: 23)
(N-dec)-TPDINPAWYASRGIRPVGRF-NH2;
                                         (SEQ ID NO: 24)
(N-dodec)-TPDINPAWYASRGIRPVGRF-NH2;
                                         (SEQ ID NO: 25)
X1'-SRAHQHS Nle ETRTPDINPAWYTGRGIRPVGRF-NH2;
                                         (SEQ ID NO: 26)
X1-SRAHQHS Nle ETRTPDINPAWYTGRGIRPVGR 1-Nal-NH2;
                                         (SEQ ID NO: 27)
X1-SRAHQHS Nle ETRTPDINPAWYTGRGIRPVGR PheCl2-NH2;
                                         (SEQ ID NO: 28)
X1-SRAHQHS Nle ETRTPDINPAWYTGRGIRPVGR PheNO2-NH2;
                                         (SEQ ID NO: 29)
X1-SRAHQHS Nle ETRTPDINPAWYTGRGIRPVGR PheF5-NH2;
                                         (SEQ ID NO: 30)
X1-SRAHQHS Nle ETRTPDINPAWYTGRGIRPVGRY-NH2;
                                         (SEQ ID NO: 31)
X1-SRAHRHS Nle EIRTPDINPAWYASRGIRPVGRY-NH2;
                                         (SEQ ID NO: 32)
(N-myr)-Nle-ETRTPDINPAWYTGRGIRPVGRF-NH2;
                                         (SEQ ID NO: 33)
(N-myr)-QHSMETRTPDINPAWYTGRGIRPVGRF-NH2;
and
                                         (SEQ ID NO: 34)
(N-myr)-QHSMETRTPDINPAWYASRGIRPVGRF-NH2;
``` wherein X=$X^1$ or $X^{1'}$, wherein. $X^{1'}$ is palmitic acid, myristic acid or stearic acid; and wherein $X^1$ is palmitic acid or myristic acid.

Disclosed herein in certain embodiments is a lipidated analog of prolactin releasing peptide (PrRP) having the formula:

```
                          (Formula 1; SEQ ID NO: 1)
                J-rRPsGRt-NH2,
``` wherein
 r is isoleucine, alanine, or phenylglycine;
 s is valine or phenylglycine; and
 t is phenylalanine, tryptophan, pyroglutamic acid, or an amino acid with a side chain containing $CH_2$—Ar or $CH_2$—S—$CH_2$—Ar, wherein Ar represents phenyl or naphthyl, optionally substituted by a halogen, methyl or nitro group;
 J represents a chain of 13 or 24 amino acids lipidated in one position by X, where X=$X^1$ or $X^2X^1$;
 wherein $X^1$ is a C8-C18 fatty acid bound to an amino acid having at least one free amino group, SH group, or OH group either directly or through $X^2$;
 and wherein $X^2$ is a hydrophilic linker selected from the group consisting of a polyoxyethylene moiety, an arylalkyl moiety, and a saturated or unsaturated, linear or branched C3-C8 hydrocarbon chain, wherein one or more carbon atoms may be replaced by one or more heteroatoms selected from the group consisting of N, S, and O; said hydrocarbon chain carrying at least one amino group or carboxylic acid group, one of which can be substituted to form CONH$_2$;
NH-polyoxyethylene;
COOM$^1$; wherein M$^1$ is alkali metal;
CN;
COOR$^1$, COR$^1$, CONHR$^1$; wherein R$^1$ is lower alkyl, aryl alkyl, polyoxyethylene, methylpolyoxyethylene, or aminoethylpolyoxyethylene;
(CHOH)nR$^2$; wherein R$^2$ is H or COOH and n is an integer from 2 to 10; or
(CH)nN+(R')$_3$; wherein each R' is independently H or C1-C4 alkyl,
with the proviso that when X is bound to the N-terminal amino acid of formula 1, then X is X$^2$X$^1$.

In some embodiments, the lipidated analog of prolactin releasing peptide (PrRP) has the formula:

(Formula 2; SEQ ID NO: 2)
(X)kRmHnHSqEuRTPDINPAWYmoRprRPsGRt-NH$_2$, wherein
k is serine, threonine or diaminopropionic acid;
m is threonine, alanine or methylalanine;
n is glutamine or arginine;
q is methionine or norleucine;
u is threonine or isoleucine;
o is glycine or serine;
p is glycine, alanine, proline, or N-methylglycine;
r is isoleucine, alanine, or phenylglycine;
s is valine or phenylglycine;
t is phenylalanine, tryptophan, pyroglutamic acid, or an amino acid with a side chain containing CH$_2$—Ar or CH$_2$—S—CH$_2$—Ar, where Ar represents phenyl or naphthyl, optionally substituted by halogen, methyl, or nitro group.

In some embodiments, the lipidated analog of prolactin releasing peptide (PrRP) has the formula: (X)kRmH-nHSqEuRTPDINPAWYmoRprRPsGRt-NH$_2$ (Formula 2; SEQ ID NO: 2), wherein kRmHnHSqEuRTPDIN-PAWYmoRp (SEQ ID NO: 35) is shortened by eliminating 1 to 11 amino acids.

In some embodiments, the lipidated analog of prolactin releasing peptide (PrRP) has the formula (X)kRmH-nHSqEuRTPDINPAWYmoRprRPsGRt-NH$_2$ (Formula 2; SEQ ID NO: 2), wherein kRmHnHsqEuRTPDIN-PAWYmoRp (SEQ ID NO: 35) is shortened by eliminating 1 to 11 amino acids from its N-terminus or its C-terminus.

In some embodiments, lipidated analog of prolactin releasing peptide (PrRP) has the formula (X)kRmH-nHsqEuRTPDINPAWYmoRprRPsGRt-NH$_2$ (Formula 2; SEQ II) NO: 2), wherein kRmHnHsqEuRTPDIN-PAWYmoRp (SEQ ID NO: 35) is shortened by eliminating 1 to 11 amino acids from its N-terminus.

In some embodiments, the lipidated analog of prolactin releasing peptide (PrRP) has the formula (X)kRmH-nHsqEuRTPDINPAWYmoRprRPsGRt-NH$_2$ (Formula 2; SEQ ID NO: 2), wherein kRmHnHsqEuRTPDIN-PAWYmoRp (SEQ ID NO: 35) is shortened by eliminating 1 to 11 amino acids from its C-terminus.

In some embodiments, the lipidated analog of prolactin releasing peptide (PrRP) has the formula:

(Formula 2; SEQ ID NO: 2)
(X)kRmHnHSqEuRTPDINPAWYmoRprRPsGRt-NH$_2$,
or (Formula 3; SEQ ID NO: 3)
(X)TPDINPAWYmoRprRPsGRt-NH$_2$;

wherein
k is serine, threonine, or diaminopropionic acid;
m is threonine, alanine, or methylalanine;
n is glutamine or arginine;
q is methionine or norleucine;
u is threonine or isoleucine;
o is glycine or serine;
p is glycine, alanine, proline, or N-methylglycine;
r is isoleucine, alanine, or phenylglycine;
s is valine or phenylglycine;
t is phenylalanine, tryptophan, pyroglutamic acid, or an amino acid with a side chain containing CH2-Ar or CH2-S—CH2-Ar, where Ar represents phenyl or naphthyl, optionally substituted by halogen, methyl or nitro group.

In some embodiments, the lipidated analog of prolactin releasing peptide (PrRP) has the formula J-rRPsGRt-NH$_2$ (Formula 1; SEQ ID NO: 1), wherein the binding affinity of said lipidated analog of prolactin releasing peptide (PrRP) towards GPR10 receptor expressed in rat hypophyseal cells is not higher than $10^{-6}$ mol·l$^{-1}$.

In some embodiments, the lipidated analog of prolactin releasing peptide (PrRP) has the formula:

(Formula 4; SEQ ID NO: 4)
(X)SRmHnHSqEuRTPDINPAWYmoRprRPsGRt-NH$_2$;

wherein
m is threonine, alanine, or methylalanine;
n is glutamine or arginine;
q is methionine or norleucine;
u is threonine or isoleucine;
o is glycine or serine;
p is glycine, alanine, proline, or N-methylglycine;
r is isoleucine, alanine, or phenylglycine;
s is valine or phenylglycine;
t is phenylalanine, tryptophan, pyroglutamic acid, or an amino acid with a side chain containing CH$_2$—Ar or CH$_2$—S—CH$_2$—Ar, where Ar represents phenyl or naphthyl, optionally substituted by halogen, methyl or nitro group, wherein X=X$^1$ or X$^2$ X$^1$, and wherein X$^1$ is a C10-C18 fatty acid, In some embodiments, the lipidated analog of prolactin releasing peptide (PrRP) has the formula J-rRPsGRt-NH$_2$ (Formula 1; SEQ ID NO: 1), wherein t is selected from the group consisting of histidine, benzylhistidine, naphthylalanine, tryptophan, pyroglutamic acid, benzylcysteine, benzyl-O-glutamate, norleucine, dichlorophenylalanine, tetrachlorophplylalanine, pentafluorophenylalanine, methyl-O-phenylalanine, methyl-NH-phenylalanine and nitrophenyalanine.

In some embodiments, the lipidated analog of prolactin releasing peptide (PrRP) has the formula:

(Formula 5; SEQ ID NO: 5)
(X)TPDINPAWYmoRGrRPsGRF-NH$_2$;

(Formula 6; SEQ ID NO: 6)
(X)TPDINPAWYmoRGrRPsGR1-Nal-NH$_2$;
or (Formula 7; SEQ ID NO: 7)
(X)RmHnHSNleETRTPDINPAWYmoRGrRPsGR1-Nal-NH$_2$;

wherein
1-nal is naphthylalanine;
m is threonine, alanine, or methylalanine;
n is glutamine or arginine;

o is glycine or serine;
r is isoleucine, alanine, or phenylglycine; and
s is valine or phenylglycine.

In some embodiments, the lipidated analog of prolactin releasing peptide (PrRP) has the formula:

(X) TPDINPAWYASRGIRPVGRF-NH$_2$,    (Formula 10; SEQ ID NO: 10)

or (X) SRTHRHSMEIRTPDINPAWYASRGIRPVGRF-NH$_2$;    (Formula 8; SEQ ID NO: 8)

wherein X=X$^1$ or X$^2$ X$^1$, wherein X$^1$ is a C12 to C16 fatty acid bound to an amino acid of formula 8 or formula 10, either directly by an amide bond or through X$^2$, and wherein X$^2$ is selected from the group consisting of β-alanine, γ-amino butyric acid, polyoxyethylene and γ-glutamic acid.

In some embodiments, the lipidated analog of prolactin releasing peptide (PrRP) has the formula:

(X) TPDINPAWYASRGIRPVGRF-NH$_2$,    (Formula 10; SEQ ID NO: 10)

or (X) SRTHRHSMEIRTPDINPAWYASRGIRPVGRF-NH$_2$,    (Formula 8; SEQ ID NO: 8)

wherein X=X$^1$ or X$^2$ X$^1$, wherein X$^1$ is bound to any one of amino acids 1 to 22 of formula 8, or 1 to 12 of formula 10, either directly or through X$^2$, and wherein said amino acid bound to X$^1$ is replaced by lysine.

In some embodiments, the lipidated analog of prolactin releasing peptide (PrRP) has the formula:

(X) TPDINPAWYASRGIRPVGRF-NH2,    (Formula 10; SEQ ID NO: 10)

or (X) SRTHRHSMEIRTPDINPAWYASRGIRPVGRF-NH2,    (Formula 8; SEQ ID NO: 8)

wherein X=X$^1$ or X$^2$ X$^1$, wherein X$^1$ is bound to amino acid 1 or 11 of formula 8, or amino acid 1 or 5 of formula 10, either directly or through X$^2$, and wherein said amino acid bound to X$^1$ is replaced by lysine.

In some embodiments, the lipidated analog of prolactin releasing peptide (PrRP) has the formula:

(X) TPDINPAWYASRGIRPVGRF-NH$_2$;    (Formula 10; SEQ ID NO: 10)

or (X) SRTHRHSMEIRTPDINPAWYASRGIRPVGRF-NH2,    (Formula 8; SEQ ID NO: 8)

wherein X=X$^1$ or X$^2$X$^1$, wherein X$^1$ is myristic acid or palmitic acid, wherein X$^1$ is bound to amino acid 1, 11 or 18 of formula 8, or 1, 5 or 7 of formula 10, either directly or through X$^2$, and wherein X$^2$ is γ-glutamic acid or polyoxyethylene, In some embodiments, the lipidated analog of prolactin releasing peptide (PrRP) has the formula:

(X) TPDINPAWYASRGIRPVGRF-NH$_2$;    (Formula 10; SEQ ID NO: 10)

or (X) SRTHRHSMEIRTPDINPAWYASRGIRPVGRF-NH$_2$,    (Formula 8; SEQ ID NO: 8)

wherein X=X$^1$ or X$^2$X$^1$, wherein X$^1$ is myristic or palmitic acid, wherein X$^1$ is bound to amino acid 1 or 11 of formula 8, or for 5 of formula 10, either directly or through X$^2$, and wherein X$^2$ is γ-glutamic acid or polyoxyethylene.

In some embodiments, the lipidated analog of prolactin releasing peptide (PrRP) is selected from the group consisting of:

SRTHRHSMEIK(palm)TPDINPAWYASRGIRPVGRF—NH$_2$;    (SEQ ID NO: 12)

TPDINPK(palm)WYASRGIRPVGRF—NH$_2$;    (SEQ ID NO: 13)

SRTHRHSMEIKTPDINPAWYASRGIRPVGRF—NH$_2$; and    (SEQ ID NO: 14)
|
X$^2$(palm)

TPDINPKWYASRGIRPVGRF—NH$_2$;    (SEQ ID NO: 15)
|
X$^2$(palm)

wherein palm is palmitic acid, and wherein X$^2$ is γ-glutamic acid or polyoxyethylene.

Additional embodiments relate to a medicament (or a pharmaceutical composition, e.g., a pharmaceutical composition comprising a lipidated analog of prolactin releasing peptide (PrRP) having the general formula: J-rRPsGRt-NH$_2$ (Formula 1; SEQ ID NO: 1), as an active ingredient), and a pharmaceutically acceptable carrier thereof. Further embodiments relate to a method of treating or preventing a medical condition characterized by elevated blood sugar by administering the medicament or pharmaceutical composition. In some embodiments the method of treating or preventing a medical condition characterized by elevated blood sugar is by peripheral administration of the medicament or pharmaceutical composition comprising a lipidated analog of prolactin releasing peptide (PrRP) having the general formula J-rRPsGRt-NH$_2$ (Formula 1; SEQ ID NO: 1).

BRIEF DESCRIPTION OF THE DRAWINGS

The following is a brief description of the drawings, which are presented for the purposes of illustrating the exemplary embodiments disclosed herein, and to present selected experimental bases for the lipidated analog of prolactin releasing peptide (PrRP)s described herein, and not for the purposes of limiting the same.

FIG. 1A illustrates glucose levels over time, while FIG. 1B illustrates Area Under Curve (AUC) through time of 30 min.

FIG. 2A illustrates resulting glucose levels over time, and FIG. 2B illustrates Area Under Curve (AUC) through 180 min.

FIG. 5A illustrates resulting changes in glucose levels (delta glucose) over time, and FIG. 5B illustrates Area Under Curve (AUC) through 180 min.

DETAILED DESCRIPTION

Figure 1A:
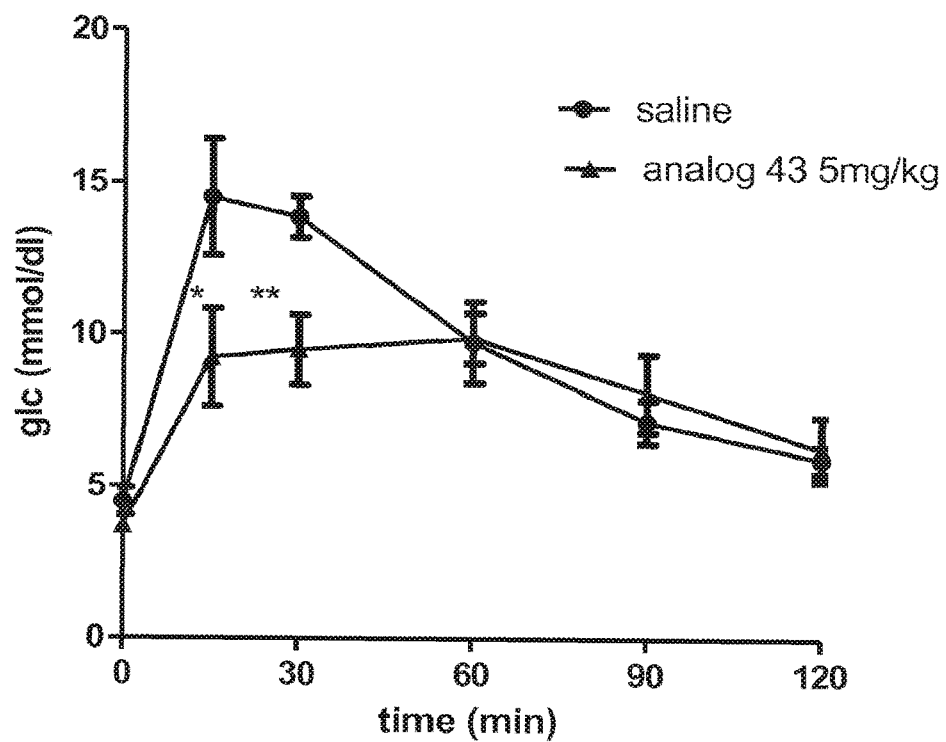
FIGS. 1A and 1B illustrate the results of intraperitoneal glucose tolerance tests (IPGTT) after acute administration of palm-PrRP31 (analog 43) and of control saline in lean mice. IPGTT was performed in overnight fasted male C57BL/6 mice. Blood glucose levels were measured at the beginning and after subcutaneous (SC—beneath the skin) administration of palm-PrRP31 (analog 43) (5 mg/kg SC) or saline (n=7) at times 30, 60, 90 and 120 min.

Disclosed herein are compositions (e.g, lipidated analogs of prolactin-releasing peptide (PrRP) and pharmaceutical compositions thereof) and using such compositions to treat subjects diagnosed as having or being susceptible to a metabolic condition, such as one or more disorders characterized by an increased level of glucose. Studies described herein demonstrate that lipidated forms of PrRP20 and PrRP31 analogs exhibited a glucose lowering effect and anorexigenic characteristics. Furthermore, studies described herein demonstrate these lipidated analogs were efficacious when administered peripherally (e.g. subcutaneously).

As described herein, the anorexigenic characteristic of PrRP lipidated analogs was established using the rat pituitary cell line RC-4B/C and the Chinese hamster ovary (CHO) cell line. This characteristic was further demonstrated in rodent studies described herein, in which the lipidated analogs were shown to decrease food intake in fasted mice in a dose-dependent manner. Further, studies described herein on several subgroups (e.g. lean mice, obese diabetic monosodium-glutamate mice, diabetic db/db mice and lean rats) showed decreased glucose levels upon administration of a lipidated PrRP analog. These results indicate that the lipidated PrRP analogs are applicable for use as novel therapeutic candidates. Furthermore, their peripheral administration through the hypothalamus and brain stem presents an advantageous alternative for delivery across the blood brain barrier. As disclosed herein, in certain embodiments, the lipidated PrRP analogs are particularly applicable for treating elevated blood glucose levels and other medical conditions associated with it.

Certain Terminologies

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The term "peptide" as used herein refers to a compound composed of at least five constituent amino acids connected by peptide (amide) bonds. The amino acids may be naturally occurring amino acids encoded by the genetic code, naturally occurring natural amino acids which are not encoded by the genetic code, and/or synthetic amino acids.

The term "analog" in reference to a peptide refers to a modified peptide, wherein one or more amino acid residues of the peptide have been substituted by other amino acid residues, and/or wherein one or more amino acid residues have been deleted from the peptide, and/or wherein one or more amino acid residues have been added to the peptide. The analog may be lipidated.

The term "treatment of a disease" as used herein refers to the management and care of a patient having developed the disease, condition or disorder. The purpose of treatment is to combat the disease, condition or disorder. Treatment includes the administration of the active compound to eliminate or control the disease by any known applicable method. Treatment of a condition or disorder can also include alleviating the symptoms or complications associated with the disease, condition or disorder.

The term "fatty acid" as used herein refers to a carboxylic acid with a long aliphatic tail (chain). For example, carboxylic acids having tails from 13 to 21 carbons long, or over 13 or over 15 carbons long.

The term "tower alkyl" as used herein denotes a C1-C6 linear or C3-C6 branched alkyl chain.

The "arylalkyl" as used herein denotes a hydrocarbon group comprising 6-12 carbon atoms and comprising at least one aromatic cycle, which can be unsubstituted, or can be substituted by 1-5 substituents selected from a group comprising —OH, —SH, a halogen, $C_1$-$C_6$ alkyl, —$NH_2$, —CN, —$NO_2$, and —COOR", wherein R" is H or $C_1$-$C_6$ alkyl.

A "polyoxyethylene" denotes an oligomer or polymer of ethylenoxide having the general formula HO—($CH_2$—$CH_2$—O)$_n$—H.

The term "salt" as used herein may be a basic salt, an acid salt, or a neutral salt. Useful salts may be formed with added cations or anions that react with anionic or cationic groups of the active molecule, respectively. These groups may be situated in the peptide chain, and/or in the side chain of the lipidated analog.

An "ester" of the lipidated analog used herein may be formed by the reaction of a free carboxylic acid group with an alcohol or a phenol, which leads to replacement of at least one hydroxyl group by an alkoxy or aryloxy group.

An "amide" of the lipidated analog used herein may be formed by a reaction of an activated form of a free carboxylic acid group with an amine or a substituted amine, or by reaction of a free or substituted amino group with an activated form of a carboxylic acid.

The term "binding affinity" used herein characterizes the interaction of most ligands with their respective binding sites. Typically, high-affinity ligand binding results from greater intermolecular force between the ligand and its receptor, and conversely low-affinity ligand binding involves less intermolecular force between the ligand and its receptor. As a general rule, high-affinity binding involves a longer residence time for the ligand at its receptor binding site than with low-affinity binding. High-affinity binding of ligands to receptors is often physiologically important when some of the binding energy can be used to cause a conformational change in the receptor, resulting in altered behavior of an associated ion channel or enzyme.

The term "agonist" used herein refers to a ligand that can bind to a receptor and trigger a physiological response. Agonist binding to a given type of receptor can be characterized both in terms of how much physiological response can be triggered and in terms of the concentration of the agonist that is required to produce the physiological response. High-affinity ligand binding implies that a relatively low concentration of a ligand is adequate to maximally occupy a ligand-binding site and trigger a physiological response. The lower the $K_i$ value is, the more likely it is that there will be a chemical reaction between the molecule and the receptive antigen. Low-affinity binding (high $K_i$ value) implies that a relatively high concentration of a ligand is required before the binding site is maximally occupied and the maximum physiological response to the ligand is achieved. $K_i$ may be quantified for a given putative agonist, for example, by competitive binding assays. For example, the binding affinity of an analog or otherwise modified version of a natural agonist might be gauged by competitive binding with the natural agonist.

Abbreviations used in this disclosure include analysis of variance (ANOVA); bovine serum albumin (BSA); bovine pancreatic trypsin inhibitor (BPTI); epidermal growth factor (EGF); 4-(2-hydroxyethyl)-1-piperazineethansulfonic acid (HEPES); phosphate buffer saline (PBS); sodium dodecyl sulfate (SDS); Tris-buffered saline (TBS); diaminopropionic acid (Dpr); 1-naphthylalanine (1-Nal); norleucine (Nle); myristoyl (myr); palmitoyl (palm); octanoyl (oct), dodecanoyl (dodec); and tridecanoyl (tridec), γ-aminobutyric acid (GABA), gamma-glutamic acid (γE), polyoxyethylene (POE), particularly 1,13-diamino-4,7,10-trioxatridecan-succinamic acid.

Prolactin-Releasing Peptide (PrRP)

Prolactin-releasing peptide (PrRP) is a neuropeptide that affects regulation of energy metabolism (Hinuma, S., et al. "A prolactin-releasing peptide in the brain," Nature 393: 272-276, 1998). There are two particularly important forms of PrRP, one is composed of 31 amino acids (PrRP31) and the second is composed of 20 amino acids (PrRP20) (Hinuma et al., 1998).

Several biological functions of PrRP have been characterized in the body. One function was ascribed to the stimulation of prolactin release Hinuma et al, 1998). Subsequently, in another study, it was found that this effect was not present in male rats, and thus the study indicated that it was not the primary function of PrRP (Jarry, H., et al., "Prolactin-releasing peptides do not stimulate prolactin release in vivo," Neuroendocrinology, 71:262-267, 2000). Upon finding PrRP in the hypothalamic paraventricular and dorsomedial nuclei (PVN and DMN) of the hypothalamus, which are important for maintaining the metabolic equilibrium, PrRP is considered as a factor affecting food intake (Lawrence, C., at al., "Alternative role for prolactin-releasing peptide in the regulation of food intake," Nat. Neurosci, 3:645-646, 2000).

Further studies on knockout mice, where the PrRP gene was deleted, indicated a role of PrRP in Hyperplagia, a condition associated with excessive hunger or increased appetite. While the frequency of individual meals was not affected, the amount of food intake in each meal was increased. Lowered energy output was not observed in these mice as body temperature and oxygen consumption were comparable to the control animals (Takayanagi et al.; Mochiduki, A., et al., "Stress response of prolactin releasing peptide knockout mice as to glucocorticoid secretion," J Neuroendocrinol, 22:576-584, 2010).

Similarly, mice lacking the gene for PrRP's receptor GPR10 had higher food intake leading to obesity. The effect was more pronounced in the female mice (Gu, W., et al., "The prolactin releasing peptide receptor (GPR10) regulates body weight homeostasis in mice," J Mol Neurosci, 22:93-103, 2004; Bjursell et al., 2007). In addition, increased food intake in the GPR10 knock-out (KO) mice was not reduced after the administration of cholecystokinin (CCK). This finding supports the hypothesis that the GPR10-PrRP system may have a key role in the signal transfer of CCK, a peripheral peptide that induces satiety sensation during food intake (Bechtold D, et al., "Prolactin-releasing peptide mediates cholecystokinin induced satiety in mice," Endocrinology, 147:4723-4729, 2006).

Structurally, mutation of amino acid residue arginine at position 30 of PrRP leads to a loss of receptor binding activity and of biological activity. Furthermore, for binding of PrRP to the receptor GPR10, position 31 requires to be phenylalanine or other amino acid with an aromatic moiety bound to at least one CH2 group of the side chain of the amino acid (Boyle, R., et al., "Structure activity studies on prolactin releasing peptide (PrRP). Analogues of PrRP (19 31) peptide," J Pept Sci, 11:161-165, 2005).

For binding experiments with PrRP analogs, radiolabeled PrRP with $^{125}$I on the tyrosine in position 20 was utilized (Satoh, F., et al., "Characterization and distribution of prolactin releasing peptide (PrRP) binding sites in the rat-evidence for a novel binding site subtype in cardiac and skeletal muscle," Br. J. Pharmacol., 129:1787-1793, 2000). It was confirmed that the monoiodation of tyrosine does not affect PrRP binding to the receptor (Maixnerová, J., et al., 2011). Amino acid modifications were introduced to the natural PrRP20 such that its biological activity was comparable to PrRP31 (Langmead, C., et al., "Characterization of the binding of [$^{125}$I] human prolactin releasing peptide (PrRP) to GPR10, a novel G protein coupled receptor," Br. J. Pharmacol., 131:683-688, 2000; Maixnerová et al., 2011; Maletínská, L., et al., "Biological properties of prolactin releasing peptide analogues with a modified aromatic ring of a C terminal phenylalanine amide," Peptides, 32:1887-1892, 2011). C-terminal phenylalanine was replaced by noncoded amino acids, phenylalanine derivatives PheCl2, PheF5 and PheNO2, or by non-coded amino acids with bulky naphthylalanine 1-Nal and 2-Nal, or by tyrosine. All analogs had conserved C-terminal amides, which is necessary for biological activity (Hinuma et al. 1998; Roland, B., et al., "Anatomical distribution of prolactin releasing peptide and its receptor suggests additional functions in the central nervous system and periphery," Endocrinology, 140:5736-5745, 1999) and, in addition, were acetylated at the N-terminus of the peptide chain to increase its stability, especially for the in vivo experiments. Biological activity was not dependent on the substitution of amino acids in positions before the C-terminal heptapeptide.

The PrRP20 analogs [Tyr31]PrRP20, [1-Nal31]PrRP20, [PheF531]PrRP20, [PheCl231]PrRP20 and [PheNO231] PrRP20 bind to the pituitary cell line RC-4B/C, which expresses the receptor GPR10, producing on the order of tens of thousands of binding sites per cell (Maixnerová et al., 2011). Those analogues exhibit $K_d$ values comparable to those for PrRP31 and PrRP20 (Maletínská et al., 2011). In addition, incubation of the RC-4B/C cells with the analogs mentioned above resulted in increased phosphorylation of the enzymes mitogen activated phosphorylase/extracellular-regulated kinase (MAPK/ERK1/2) and the cAMP response element-binding protein (CREB). The analogs also stimulated the release of prolactin into the medium, with EC50 values comparable to that of PrRP20 (Hinuma et al., 1998). These analogs of PrRP, upon intracerebroventricular (ICV— into the ventricular system of the brain) administration in the dose of 10 nmol, caused statistically significant reduction of food intake in fasted mice (Maletíinská et al., 2011).

Lipidated Analogs of PrRP20 and PrRP31

Disclosed herein are compositions (e.g, lipidated analogs of prolactin-releasing peptide and pharmaceutical compositions thereof) and methods of treating subjects diagnosed as having or being susceptible to one or more disorders characterized by an increased level of glucose in blood with such compositions.

The pharmacological effects of these compounds in vitro and in vivo are described herein, as well as their applications in treating conditions such as type 2 diabetes and related conditions, such as obesity and eating disorders. Also described herein is the demonstration that peripheral administration of various lipidated analogs of prolactin releasing peptide (PrRP)s lowers blood glucose levels, which can be useful for treating impaired glucose tolerance (IGT) and glucose intolerance condition.

Disclosed herein, in certain embodiments, are lipidated analogs of PrRP20 or PrRP31, 20 or 31 amino acids in length, respectively, comprising the preferred heptapeptide sequence IRPVGRF-NH$_2$ (SEQ ID NO: 36) at the C-terminus. In some embodiments, at the free functional group of any of the amino acids in the peptide chain, preferably an amino acid other than amino acids of the sequence IRPVGRF-NH$_2$ (SEQ ID NO: 36) and the N-terminal amino acid, a C8 to C18 fatty acid is either directly bound by an amide bond, or is bound through a hydrocarbyl or polyoxyethylene spacer. In some embodiments, in the C-terminus heptapeptide sequence, isoleucine may be substituted by phenylglycine or alanine, and valine may be substituted by phenylglycine. In some embodiments, the terminal phenylalanine is replaced by tryptophan, pyroglutamic acid or an amino acid with a side chain containing CH$_2$—Ar or CH$_2$—S—CH$_2$—Ar, where Ar represents phenyl or naphthyl, optionally substituted by a halogen, methyl or nitro group.

In some embodiments, lipidated PrRPs exhibited near native binding affinities toward the GPR10 receptor. In some embodiments, lipidated PrRPs reduced blood glucose when administered to mammalian organisms.

A list of exemplary synthesized PrRPs and lipidated PrRP analogs are described in Table 1.

TABLE 1

Structures of PrRP31, PrRP20, and lipidated analogs of PrRP31 and PrRP20

| SEQ ID NO: | Analog no. | Sequence |
|---|---|---|
| 37 | Rat PrRP20 | TPDINPAWYTGRGIRPVGRF-NH$_2$ |
| 38 | Human PrRP20 | TPDINPAWYASRGIRPVGRF-NH$_2$ |
| 39 | Rat PrRP31 | SRAHQHSMETRTPDINPAWYTGRGIRPVGRF-NH$_2$ |
| 40 | Human PrRP31 | SRTHRHSMEIRTPDINPAWYASRGIRPVGRF-NH$_2$ |
| 41 | 1 | (myr)TPDINPAWYTGRGIRPVGRF-NH$_2$ |
| 42 | 2 | (myr)TPDINPAWYASRGIRPVGRF-NH$_2$ |
| 43 | 3 | S RAHQHS Nle ETRTPDINPAWYTGRGIRPVGRF-NH$_2$ |
| 44 | 4 | (N-oct)SRAHQHS Nle ETRTPDINPAWYTGRGIRPVGRF-NH$_2$ |
| 45 | 5 | (N-dec)SRAHQHS Nle ETRTPDINPAWYTGRGIRPVGRF-NH$_2$ |
| 46 | 6 | (N-dodec)SRAHQHS Nle ETRTPDINPAWYTGRGIRPVGRF-NH$_2$ |

TABLE 1-continued

Structures of PrRP31, PrRP20, and lipidated analogs of PrRP31 and PrRP20

| SEQ ID NO: | Analog no. | Sequence |
|---|---|---|
| 47 | 7 | (N-myr)SRAHQHS Nle ETRTPDINPAWYTGRGIRPVGRF-NH$_2$ |
| 48 | 8 | (N-palm)SRAHQHS Nle ETRTPDINPAWYTGRGIRPVGRF-NH$_2$ |
| 49 | 9 | (N-stear)SRAHQHS Nle ETRTPDINPAWYTGRGIRPVGRF-NH$_2$ |
| 50 | 10 | SRAHQHS Nle ETRTPDINPAWYTGRGIRPVGR 1-Nal-NH$_2$ |
| 51 | 11 | (N-myr)SRAHQHS Nle ETRTPDINPAWYTGRGIRPVGR 1-Nal-NH$_2$ |
| 52 | 12 | (N-palm)SRAHQHS Nle ETRTPDINPAWYTGRGIRPVGR 1-Nal-NH$_2$ |
| 53 | 13 | SRAHQHS Nle ETRTPDINPAWYTGRGIRPVGR PheCl$_2$—NH$_2$ |
| 54 | 14 | (N-myr)SRAHQRS Nle ETRTPDINPAWYTGRGIRPVGR PheCl$_2$—NH$_2$ |
| 55 | 15 | (N-palm)SRAHQHS Nle ETRTPDINPAWYTGRGIRPVGR PheCl$_2$—NH$_2$ |
| 56 | 16 | SRAHQHS Nle ETRTPDINPAWYTGRGIRPVGR PheNO$_2$—NH$_2$ |
| 57 | 17 | (N-myr)SRAHQHS Nle ETRTPDINPAWYTGRGIRPVGR PheNO$_2$—NH$_2$ |
| 58 | 18 | (N-palm)SRAHQHS Nle ETRTPDINPAWYTGRGIRPVGR PheNO$_2$—NH$_2$ |
| 59 | 19 | SHQRPADTHWYPRG Nle FPTIGRITARNGEVSR |
| 60 | 20 | (N-myr)SHQRPADTHWYPRG Nle FPTIGRITARNGEVSR |
| 61 | 21 | SRAHQHS Nle ETRTPDINPAWYTGRGIRPVGR PheF$_5$—NH$_2$ |
| 62 | 22 | (N-palm)SRAHQHS Nle ETRTPDINPAWYTGRGIRPVGR PheF$_5$—NH$_2$ |
| 63 | 23 | SRAHQHS Nle ETRTPDINPAWYTGRGIRPVGR Tyr-NH$_2$ |
| 64 | 24 | (N-palm)SRAHQHS Nle ETRTPDINPAWYTGRGIRPVGR Tyr-NH$_2$ |
| 65 | 25 | D-Phe-D-Arg-GVPRIGRGTYWAPNIDPT-NH$_2$ |
| 66 | 26 | (N-myr) D-Phe-D-Arg-GVPRIGRGTYWAPNIDPT-NH$_2$ |
| 67 | 27 | TPDINPAWYTGR Sar IRPVGRF-NH$_2$ |
| 68 | 28 | (N-myr)TPDINPAWYTGR Sar IRPVGRF-NH$_2$ |
| 69 | 29 | TPDINPAWY N-Me-Ala SRGIRPVGRF-NH$_2$ |
| 70 | 30 | (N-myr)TPDINPAWY N-Me-Ala SRGIRPVGRF-NH$_2$ |
| 71 | 31 | TPDINPAWYTGRGARPFGRF-NH$_2$ |
| 72 | 32 | (N-myr)TPDINPAWYTGRGARPFGRF-NH$_2$ |
| 73 | 33 | TPDINPAWYASRPFRPVGRF-NH$_2$ |
| 74 | 34 | (N-myr)TPDINPAWYASRPFRPVGRF-NH$_2$ |
| 75 | 35 | Nle-ETRTPDINPAWYTGRGIRPVGRF-NH$_2$ |
| 76 | 36 | (N-myr)Nle-ETRTPDINPAWYTGRGIRPVGRF-NH$_2$ |
| 77 | 37 | QHSMETRTPDINPAWYTGRGIRPVGRF-NH$_2$ |
| 78 | 38 | (N-myr)QHSMETRTPDINPAWYTGRGIRPVGRF-NH$_2$ |
| 79 | 39 | (N-oct)TPDINPAWYASRGIRPVGRF-NH$_2$ |
| 80 | 40 | (N-dec)TPDINPAWYASRGIRPVGRF-NH$_2$ |
| 81 | 41 | (N-dodec)TPDINPAWYASRGIRPVGRF-NH$_2$ |
| 82 | 42 | (N-myr)SRTHRHSMEIRTPDINPAWYASRGIRPVGRF-NH$_2$ |
| 83 | 43 | (N-palm)SRTHRHSMEIRTPDINPAWYASRGIRPVGRF-NH$_2$ |

TABLE 1-continued

Structures of PrRP31, PrRP20, and lipidated analogs of PrRP31 and PrRP20

| SEQ ID NO: | Analog no. | Sequence |
|---|---|---|
| 84 | 44 | (N-palm)SRTHRHSMEIRTPDINPAWYASRGIRPVGRF-NHMe |
| 85 | 45 | (N-palm)SRTHRHSMEIRTPDINPAWYASRGIRPVGRF-NOMe |
| 86 | 46 | (N-myr)SRAHQHSMETRTPDINPAWYTGRGIRPVGRF-NH$_2$ |
| 87 | 47 | (N-palm)SRAHQHSMETRTPDINPAWYTGRGIRPVGRF-NH$_2$ |
| 88 | 48 | SRTHRHSMEIK(N-palm)TPDINPAWYASRGIRPVGRF-NH$_2$ |
| 89 | 49 | TPDIK(N-palm)PAWYASRGIRPVGRF-NH$_2$ |
| 90 | 50 | TPDINPK(N-palm)WYASRGIRPVGRF-NH$_2$ |
| 91 | 51 | SRTHRHSMEIRTPDINPK(N-palm)WYASRGIRPVGRF-NH$_2$ |
| 92 | 52 | SRTHRHSMEIK(N-γE(N-palm))TPDINPAWYASRGIRPVGRF-NH$_2$ |
| 93 | 53 | SRTHRHSMEIK(N-GABA(N-palm))TPDINPAWYASRGIRPVGRF-NH$_2$ |
| 94 | 54 | (N-palm)γ-ESRTHRHSMEIRTPDINPAWYASRGIRPVGRF-NH$_2$ |
| 95 | 55 | SETHRHSMEIK(N-γE(N-palm))TPDINPAWYASRGIRPVGRF-NH$_2$ |
| 96 | 56 | SETHEHSMEIK(N-γE(N-palm))TPDINPAWYASRGIRPVGRF-NH$_2$ |
| 97 | 57 | SRTHRHSMEIK(N-palm(N-POE))TPDINPAWYASRGIRPVGRF-NH$_2$ |
| 98 | 58 | SETHRHSMEIK(N-POE(N-palm))TPDINPAWYASRGIRPVGRF-NH$_2$ |
| 99 | 59 | (N-palm(N-POE))SRTHRHSMEIK(N-palm(N-POE))TPDINPAWYASRGIRPVGRF-NH$_2$ |

GABA—γ-aminobutyric acid,
POE—poly(oxyethylene),
γE—gamma-glutamic acid

In some embodiments, the lipidated analog of PrRP is one of SEQ ID NOs.: 41-99.

Disclosed herein, in certain embodiments, are methods for treating a subject diagnosed as having or being susceptible to one or more disorders characterized by an increased level of glucose in blood by administering a lipidated analog of PrRP, wherein the lipidated analog of PrRP is one of SEQ ID NOs: 41-99.

Disclosed herein, in certain embodiments, is a hydrophilic linker ($X^2$) between the lipid (typically a C8 to C18 fatty acid) and an amino acid (typically PrRP20, PrRP31 or an analog). In some embodiments, the linker is chosen from a polyoxyethylene moiety, an arylalkyl moiety, or single bond, optionally bivalent, linear or branched C3-C8 hydrocarbon chain. Polyoxyethylene can comprise two or more ethoxy subunits, and can optionally be terminated by an amino group or by an acetyl group. For example, ethoxy may be coupled via an amide bond.

In some embodiments, when the linker $X^2$ comprises a hydrocarbon chain, carbon atoms of the hydrocarbon chain may be replaced by heteroatoms selected from a group comprising N, S, and O. They can also be replaced by a —P(=O)($R^x$)— or —O—P(=O)(—$OR^x$)— group where $R^x$ is selected from C1-C3 alkyl, forming a phosphine oxide or phosphonate moiety. Said chain carries at least one, more preferably at least two, and preferably two amino groups or carboxylic acid groups, at least one of which can be substituted to form groups as CONH$_2$; NH-polyoxyethylene; COO$M^1$ where $M^1$ is alkali metal, preferably Na or K; CN; COO$R^1$, CO$R^1$, or CONH$R^1$ where $R^1$ is chosen from a group comprising lower alkyl, arylalkyl, polyoxyethylene, methylpolyoxyethylene, aminoethylpolyoxyethylene, (CHOH)$_n R^2$ where $R^2$ is H or COOH and n is an integer from 2 to 10, or (CH)$_n N^+$ ($R'$)$_3$, where each R' can independently be H or C1-C4 alkyl.

In some embodiments, the linker $X^2$ is bound to an amino acid of the peptide chain using its free NH$_2$, COOH, OH or SH groups, or to a lysine replacing any amino acid of the peptide chain except sequence of IRPVGR-NH$_2$ (SEQ ID NO: 36) at the C-terminus.

In some embodiments, when $X^1$ (typically a fatty acid) is described as being bound to an amino acid of the peptide chain, it may be bound to any of the amino acids in that chain unless otherwise limited, such as, for example, in the definition of J.

In some embodiments, the lipidated analogs of PrRP20 or PrRP31 described herein (e.g, the lipidated analogs of formulas 1, 2, 3 and 4) include a C-terminal amino acid selected from histidine, benzylhistidine, naphthylalanine, tryptophan, pyroglutamic acid, benzylcysteine, benzyl-O-glutamate, norleucine, dichlorophenylalanine, tetrachlorophynylalanine pentafluorophenylalanine, methyl-O-phenylalanine, methyl-NH-phenylalanine and nitrophenylalanine.

In some embodiments, are peptides in which the amino acids in positions preceding said C-terminal heptapeptide of the PrRP may not essential for the described biological activity of the lipidated analogs. The substitution of some or all of those amino acids with different amino acid is possible and contemplated. These substitutions are particularly contemplated so long as the resulting lipidated analog of prolactin releasing peptide (PrRP) has a preferred binding affinity to the PrRP receptor with K in the order of not higher than $10^{-6}$ mol·l$^{-1}$ or lower, (or preferably not higher than $10^{-7}$, or $10^{-8}$ mol·l$^{-1}$ or lower), exhibits agonist activity towards PrRP (preferably determined by MAPK/ERK1/2 signaling in RC-4B/C cells), reduces blood glucose in mammals such as rats, mice, and humans, and/or demonstrates anorexigenic activity equal to or higher than that of PrRP, preferably tested by food intake in fasted mice after central and peripheral administration.

In certain embodiments, the various lipidated analogs of PrRP20 or PrRP31 include a fatty acid which is selected from a group comprising fatty acids with 8 to 18 carbons, preferably with 10 to 18 carbon atoms, and even more preferably from 12 to 16 carbon atoms.

In some embodiments, the fatty acid has 8, 9, 10, 11, 12, 13, 14, 15, 16, 17, or 18 carbon atoms.

In some embodiments, lipidated analogs of PrRP20 and/or PrRP31 contain one or more amino acid substitution(s) in positions 2-24 of formula 2 (SEQ ID NO: 2), or in positions 2-13 of formula 3 (SEQ ID NO: 3). In some embodiments, analogs maintain sufficient binding activity and/or glucose suppressing activity. Preferably the analogs include substitutions which do not increase the $K_i$ value (increased $K_i$ value corresponds to weaker binding affinity) of the resulting lipidated analog of PrRP to GPR10 higher than $10^{-6}$ mol·l$^{-1}$, as measured in the rat hypophyseal cell line RC-4B/C grown on 24-well plates, which had their bottom coated with polyethyleneimine, up to the optimal density of 300-450 thousand cells per well. The following agents were subsequently added: binding buffer containing 20 mmol·l$^{-1}$ HEPES, pH 7.4, 118 mmol·l-1 NaCl, 4.7 mmol·l$^{-1}$ KCl, 5 mmol·l$^{-1}$ MgCl2, 5.5 mmol·l$^{-1}$ glucose, 1 mg/ml bovine serum albumin, 0.1 mg/ml bovine pancreatic trypsin inhibitor; unlabeled analogs of PrRP to a final concentration between $10^{-11}$ to $10^{-4}$ mol·l$^{-1}$, and $^{125}$I-PrRP31 at final concentration of $10^{-10}$ mol·l$^{-1}$; the plate was incubated for 60 min at room temperature and thereafter the cells were solubilized in 0.1 mol/l solution of NaOH and the radioactivity bound to the cell was counted in a γ-counter.

Some embodiments relate to the use of the lipidated analogs described herein (e.g, the lipidated analogs of PrRP20 or PrRP31, having a fatty acid bound directly to an amino acid not in position 1 or bound by a linker) as agents which lower an increased level of glucose in blood and improve related medical conditions, such as obesity and eating disorders, after peripheral administration—subcutaneous administration.).

In some embodiments, any of the lipidated analogs described herein, including lipidated analogs of PrRP20 or PrRP31 having a fatty acid bound directly to an amino acid not in position 1 or bound by a linker, are utilized as an agent for the treatment of an increased level of glucose in blood, and/or for treatment of insulin resistance.

In some embodiments, pharmaceutically acceptable salts, amides, or esters of any of the compositions described herein are utilized.

In some embodiments, the pharmaceutical compositions comprise at least one or more of the lipidated analogs described herein, including lipidated analogs of PrRP20 or PrRP31 having a fatty acid bound directly to an amino acid not in position 1 or bound by a linker, as an active ingredient.

In some embodiments, the pharmaceutical compositions are administered to a patient as a method of treating blood sugar conditions. In some embodiments, the pharmaceutical compositions are for preventing or treating a subject diagnosed with or susceptible to having disorders characterized by an increased level of glucose in blood.

Disclosed herein, in certain embodiments, are lipidated analogs of PrRP20 or PrRP31 having a general formula:

(Formula 1; SEQ ID NO: 1)
J-rRPsGRt-NH$_2$, wherein
r is isoleucine, alanine, or phenylglycine;
s is valine or phenylglycine; and
t is phenylalanine, tryptophan, pyroglutamic acid or an amino acid with a side chain containing CH$_2$—Ar or CH$_2$—S—CH$_2$—Ar, wherein Ar represents phenyl or naphthyl, optionally substituted by a halogen, methyl or nitro group, J represents a chain of 13 or 24 amino acids lipidated in one random position by the X=X$^1$ or X$^2$X$^1$; X$^1$ being C8-C18 fatty acid, which is bound to the amino acid having at least one free amino group or SH or OH group directly or through X$^2$ which is a hydrophilic linker selected from a group comprising polyoxyethylene moiety, arylalkyl moiety or saturated or unsaturated, linear or branched C3-C8 hydrocarbon chain, wherein one or more carbon atoms can be replaced by heteroatoms selected from a group comprising N, S, O, said hydrocarbon chain carrying at least one, preferably two amino groups or carboxylic acid groups, one of which can be substituted to form groups as CONH$_2$; NH-polyoxyethylene; COOM$^1$ where M1 is alkali metal, preferably Na or K; CN; COOR1, COR$^1$, or CONHR$^1$ where R$^1$ is chosen from a group including lower alkyl, arylalkyl, polyoxyethylene, methylpolyoxyethylene, aminoethylpolyoxyethylene, (CHOH)$_n$R$^2$ where R$^2$ is H or COOH and n is an integer from 2 to 10 or (CH)$_n$N+R$^3$, and in some embodiments R$^3$ can be H or C1-C4 alkyl; preferably with the proviso that when X is bound to the amino acid in position 1 of the peptide chain, then X is X$^2$X$^1$.

In some embodiments, the lipidated analogs of PrRP31 have a general formula:

(Formula 2; SEQ ID NO: 2)
(X)kRmHnHSqEuRTPDINPAWYmoRprRPsGRt-NH$_2$, wherein
k is serine, threonine or diaminopropionic acid;
m is threonine, alanine or methylalanine;
n is glutamine or arginine;
q is methionine or norleucine;
u is threonine or isoleucine;
o is glycine or serine;
p is glycine, alanine, proline or N-methylglycine;
r is isoleucine, alanine or phenylglycine;
s is valine or phenylglycine;
t is phenylalanine, tryptophan, pyroglutamic acid, or an amino acid with a side chain containing CH$_2$—Ar or CH$_2$—S—CH2-Ar, wherein Ar represents phenyl or naphthyl, optionally substituted by halogen, methyl or nitro group; and X is as described earlier, with the proviso when X is bound to the amino acid in position 1 of the peptide chain, X will be X$^2$X$^1$; and wherein the chain of amino acids kRmHnHSqEuRTPDINPAWYmoRp (SEQ II) NO: 35) is optionally shortened by eliminating from 1 to 11 amino acids.

In some embodiments, the lipidated analogs of PrRP31 have a general formula:

(Formula 2; SEQ ID NO: 2)
(X)kRmHnHSqEuRTPDINPAWYmoRprRPsGRt-NH$_2$, wherein k, m, n, q, u, o, p, r, s, t and X are as described earlier, with the proviso that when X is bound to the amino acid in position 1 of the peptide chain, X will be $X^1X^2$;

and wherein the chain of amino acids kRmHnHSqEuRTPDINPAWYmoRp (SEQ ID NO: 35) is optionally shortened from N-terminus by eliminating from 1 to 11 amino acids.

In other embodiments, the lipidated analogs of PrRP20 or PrRP31 are selected from peptides of formulas

```
                                      (Formula 2; SEQ ID NO: 2)
    (X) kRmHnHSqEuRTPDINPAWYmoRprRPsGRt-NH2,
or
                                      (Formula 3; SEQ ID NO: 3)
    (X) TPDINPAWYmoRprRPsGRt-NH2,
``` wherein k, m, n, q, u, o, p, r, s, t and X are as described earlier, with the proviso when X is bound to the amino acid in position 1 of the peptide chain, X will be $X^2X^1$.

In some embodiments, the lipidated analogs of PrRP31 have the formula:

```
                                      (Formula 4; SEQ ID NO: 4)
    (X) SRmHnHSqEuRTPDINPAWYTmoRprRPsGRt-NH2,
``` wherein m, n, q, u, o, p, r, s, t are as described earlier;

$X=X^1$ or $X^2X^1$, wherein $X^1$ is a C8-C18 fatty acid and preferably a C10-C18 fatty acid, which is bound in one random position to the original amino acid or to a replaced amino acid of the above mentioned peptide chain, either directly by an amide bond, or alternatively through $X^2$ which is as described earlier, with the proviso when X is bound to the amino acid in position 1 of the peptide chain, then X is $X^2X^1$.

In some embodiments, the lipidated analogs of PrRP20 or PrRP31 are selected from the group consisting of:

```
                                      (Formula 5; SEQ ID NO: 5)
    (X) TPDINPAWYmoRGrRPsGRF-NH2;

(Formula 6; SEQ ID NO: 6)
    (X) TPDINPAWYmoRGrRPsGR 1-Nal-NH2;
``` and (X)RmHnHSNleETRDINPAWYmoRGrPPsGR 1-Nal-NH2 (Formula 7; SEQ ID NO: 7); wherein 1-nal is naphthylalanine; m, n, o, r, s and X are as described earlier, with the proviso when X is bound to the amino acid in position 1 of the peptide chain then X is $X^2X^1$.

In some embodiments, the lipidated analog of PrRP31 is:

```
                                      (Formula 8; SEQ ID NO: 8)
    (X) SRTHRHSMEIRTPDINPAWYASRGIRPVGRF-NH2;
or
                                      (Formula 9; SEQ ID NO: 9)
    (X) SRAHQHSMETRTPDINPAWYTGRGIRPVGRF-NH2;
``` wherein X is as described earlier with the proviso when X is bound to the amino acid in position 1 of the peptide chain then X is $X^2X^1$.

In some embodiments, the lipidated analog of PrRP20 is according to the formula:

```
                                      (Formula 11; SEQ ID NO: 11)
    (X) TPDINPAWYmoRGIRPVGRF-NH2;
``` wherein m is threonine or alanine; and o is glycine or serine; X is as described earlier with the proviso that when X is bound to the amino acid in position 1 of the peptide chain, then X is $X^2X^1$.

Additional embodiments described herein relate to lipidated analogs of PrRP20 or PrRP31 according to the formula:

```
                                      (Formula 10; SEQ ID NO: 10)
    (X) TPDINRAWYASRGIRPVGRF-NH2;
or
                                      (Formula 8; SEQ ID NO: 8)
    (X) SRTHRHSMEIRTPDINPAWYASRGIRPVGRF-NH2,
``` wherein $X=X^1$ or $X^1X^2$, $X^1$ being C12 to C16 fatty acid, which is bound in one random position to the original amino acid or to the replaced amino acid of the above mentioned peptide chain directly by an amide bond or through $X^2$, which is selected from the group consisting of polyoxyethylene, β-alanine, γ-amino butyric acid and γ-glutamic acid, with the proviso that when X is bound to the amino acid in position 1 of the peptide chain, then X will be $X^2X^1$.

In some embodiments, the lipidated analogs of PrRP20 or PrRP31 are according to the formula:

```
                                      (Formula 10; SEQ ID NO: 10)
    (X) TPDINPAWYASRGIRPVGRF-NH2;
or
                                      (Formula 8; SEQ ID NO: 8)
    (X) SRTHRHSMEIRTPDINPAWYASRGIRPVGRF-NH2;
``` wherein $X=X^1$ or $X^2X^1$, $X^1$ being myristic or palmitic acid, which is bound in one random position to the original amino acid or to the replaced amino acid of the above mentioned peptide chain directly by an amide bond or through X, which is selected from the group consisting of polyoxyethylene, β-alanine, γ-amino butyric acid and γ-glutamic acid, with the proviso when X is bound to the amino acid in position 1 of the peptide chain then X is $X^2X^1$.

In some embodiments, the lipidated analogs of PrRP20 or PrRP31 are according to the formula:

```
                                      (Formula 10; SEQ ID NO: 10)
    (X) TPDINPAWYASRGIRPVGRF-NH2;
or
                                      (Formula 8; SEQ ID NO: 8)
    (X) SRTHRHSMEIRTPDINPAWYASRGIRPVGRF-NH2;
``` wherein $X=X^1$ or $X^2X^1$, $X^1$ being myristic or palmitic acid, which is bound in one random position to the original amino acid or to the replaced amino acid of the above mentioned peptide chain directly by an amide bond or through $X^2$, which is γ-glutamic acid or polyoxyethylene, with the proviso when X is bound to the amino acid in position 1 of the peptide chain then X is $X^2X^1$.

In some embodiments, the lipidated analogs of PrRP20 or PrRP31 are according to the formula:

```
                                      (Formula 10; SEQ ID NO: 10)
    (X) TPDINPAWYASRGIRPVGRF-NH2,
or
                                      (Formula 8; SEQ ID NO: 8)
    (X) SRTHRHSMEIRTPDINPAWYASRGIRPVGRF-NH2;
``` wherein X=X¹ or X²X¹, X¹ being myristic or palmitic acid, which is bound to the lysine replacing any of amino acids 1 to 22 of formula 8, or any of amino acids 1 to 12 of formula 10, either directly by an amide bond or through X² which is selected from the group consisting of polyoxyethylene, β-alanine, γ-amino butyric acid, and γ-glutamic acid, with the proviso when X is bound to the amino acid in position 1 of the peptide chain then X is X²X¹.

In some embodiments, the lipidated analog of PrRP20 or PrRP31 is according to the formula:

```
                                    (Formula 10; SEQ ID NO: 10)
  (X)TPDINPAWYASRGIRPVGRF-NH₂
or
                                    (Formula 8; SEQ ID NO: 8)
  (X)SRTHRHSMEIRTPDINPAWYASRGIRPVGRF-NH₂,
``` wherein X=X¹ or X²X¹, X¹ being myristic or palmitic acid, which is bound to the original or replaced amino acid 1 to 22 of formula 8 or 1 to 12 of formula 10, directly by an amide bond or through X², which is γ-glutamic acid or polyoxyethylene, with the proviso that when X is bound to the amino acid in position 1 of the peptide chain, then X is X²X¹.

In some embodiments, the lipidated analogs of PrRP20 or PrRP31 are according to the formula:

```
                                    (Formula 10; SEQ ID NO: 10)
  (X)TPDINPAWYASRGIRPVGRF-NH₂
or
                                    (Formula 8; SEQ NO: 8)
  (X)SWTHRHSMEIRTPDINPAWYASRGIRPVGRF-NH₂,
``` wherein X=X¹ or X²X¹, X¹ being myristic or palmitic acid, which is bound to the original or replaced amino acid in position 1, 11 or 18 of formula 8, or position 1, 5 or 7 of formula 10, directly by an amide bond or through X², which is γ-glutamic acid or polyoxyethylene, with the proviso when X is hound to the amino acid in position 1 of the peptide chain then X is X²X¹.

In some embodiments, the lipidated analogs of PrRP20 or PrRP31 are according to the formula:

```
                                    (Formula 10; SEQ ID NO: 10)
  (X)TPDINPAWYASRGIRPVGRF-NH₂
or
                                    (Formula 8; SEQ ID NO: 8)
  (X)SRTHRHSMEIRTPDINPAWYASRGIRPVGRF-NH₂,
``` wherein X=X¹ or X²X¹, being myristic or palmitic acid, which is bound to the original or replaced amino acid in position 1 or 11 of formula 8, or position 1 or 7 of formula 10, directly by an amide bond or through X², which is γ-glutamic acid or polyoxyethylene, wherein preferably when X is bound to the amino acid in position 1 of the peptide chain then X is X²X¹.

In alternative embodiments, the lipidated analogs of PrRP20 or PrRP31 are according to the formula:

```
                                    (Formula 10; SEQ ID NO: 10)
  (X)TPDINPAWYASRGIRPVGRF-NH₂;
or
                                    (Formula 8; SEQ ID NO: 8)
  (X)SRTHRHSMEIRTPDINPAWYASRGIRPVGRF-NH₂;
``` wherein X=X¹ or X²X¹, X¹ being myristic or palmitic acid, which is bound to the lysine replacing amino acid 1 or 11 of formula 8, or 1 or 7 of formula 10, directly by an amide bond or through X², which is γ-glutamic acid or polyoxyethylene.

In some embodiments, the lipidated analogs of PrRP20 or PrRP31 are according to the formula:

```
                                            (SEQ ID NO: 12)
  SRTHRHSMEIK(palm)TPDINPAWYASRGIRPVGRF-NH₂;
                                            (SEQ ID NO: 13)
  TPDINPK(palm)WYASRGIRPVGRF-NH₂;
                                            (SEQ ID NO: 14)
  SRTHRHSMEIKTPDINPAWYASRGIRPVGRF-NH₂; or
             |
             X²(palm)
                                            (SEQ ID NO: 15)
  TPDINPKWYASRGIRPVGRF-NH₂;
       |
       X²(palm)
``` wherein palm is palmitic acid and X² is γ-glutamic acid.

In alternative embodiments, the lipidated analogs of PrRP20 or PrRP31 are according to the formula:

```
                                            (SEQ ID NO: 14)
  SRTHRHSMEIKTPDINPAWYASRGIRPVGRF-NH₂; or
             |
             X²(palm)
                                            (SEQ ID NO: 15)
  TPDINPKWYASRGIRPVGRF-NH₂;
       |
       X²(palm)
``` wherein palm is palmitic acid and X² is polyoxyethylene.

Methods of Treatment

Without being bound by theory or by a particular biochemical mechanism, the characteristics of the lipidated analogs described herein are particularly useful for treating disorders characterized by an increased level of glucose in blood. Lipidation of the peptides (lipidated PrRP analogs) described herein facilitates the delivery of therapeutic peptides across the blood-brain barrier after peripheral administration. As described herein, lipidation of PrRP enables induction of central effects after peripheral administration.

A mammal can be identified as having or being likely to develop an increased level of glucose in blood using standard clinical techniques. For example, analysis of a human's family history and/or eating habits can be used to determine whether or not the human is likely to develop an increased level of glucose in blood, and thus also an increased risk of developing insulin resistance and type 2 diabetes. Direct measurement of blood glucose and related blood factors is informative. A mammal identified as having or being susceptible to developing an increased level of glucose in blood can be treated by administering one or more of the lipidated analogs disclosed herein.

Disclosed herein, in certain embodiments, are methods of using the specific and general compounds to treat or to prevent disorders caused or characterized by increased blood glucose. In some embodiments, the methods are used to treat or prevent disorders in mammals. In some embodiments, the mammal is a human.

In some embodiments, the methods include administering to a subject in need of one or more of the lipidated analogs, typically as part of a pharmaceutical composition. Such compositions typically contain a therapeutically effective amount of one or more lipidated analogs, as well as suitable excipients.

Some embodiments relate to a method of treating a subject diagnosed as having or being susceptible to one or more disorders characterized by an increased level of glucose in blood, the method comprising the step of administering to the subject a lipidated analog of prolactin-releasing peptide (PrRP) having a general formula:

(Formula 1; SEQ ID NO: 1)
J-rRPsGRt-NH$_2$, wherein
r is isoleucine, alanine, or phenylglycine;
s is valine or phenylglycine; and
t is phenylalanine, tryptophan, pyroglutamic acid or an amino acid with a side chain containing CH$_2$—Ar or CH$_2$—S—CH$_2$—Ar, wherein Ar represents phenyl or naphthyl, optionally substituted by a halogen, methyl or nitro group; and J represents a chain of 13 or 24 amino acids lipidated in one random position by either X X$^1$ or X$^2$X$^1$; X$^1$ being C8-C18 fatty acid, which is bound to an amino acid having at least one free amino group or SH or OH group directly, or alternatively through X$^2$ which is a hydrophilic linker selected from a group comprising polyoxyethylene moiety, arylalkyl moiety or saturated or unsaturated, linear or branched C3-C8 hydrocarbon chain, wherein some carbon atoms can be replaced by heteroatoms selected from a group comprising N, S, O, said chain carrying at least one, preferably two amino groups or carboxylic acid groups, one of which can be substituted to form groups as CONH$_2$; NH-polyoxyethylene; COOM$^1$ where M$^1$ is alkali metal, preferably Na or K; CN; COOR$^1$, COR$^1$, or CONHR$^1$ where R$^1$ is chosen from a group including lower alkyl, arylalkyl, polyoxyethylene, methylpolyoxyethylene, aminoethylpolyoxyethylene, (CHOH)$_n$R$^2$ where R$^2$ is H or COOH and n is an integer from 2 to 10 or (CH)$_n$N+R$_3$, where R$_3$ can be the same or different as H or C1-C4 alkyl. In some embodiments, the disorder is characterized by insulin resistance, impaired glucose-stimulated insulin release (e.g., pancreatic β-cell dysfunction) and by inappropriate secretion of glucagon. In some embodiments, the disorder is hyperglycemia or diabetes. In some embodiments, the hyperglycemia is a chronic hyperglycemia. In some embodiments, the diabetes is a type 2 diabetes. In some embodiments, the type 2 diabetes is associated with a second disorder, such as obesity, cardiovascular disease, hypertension or dyslipidemia.

Further embodiments relate to a method of preventing or treating a subject diagnosed with or susceptible to having disorders characterized by an increased level of glucose in blood, comprising the step of administering to the subject of treatment at least one lipidated analog of prolactin-releasing peptide having a general formula:

(Formula 2; SEQ ID NO: 2)
(X)kPmHnHSqEuRTPDINRAWYmoRprRPsGRt-NH$_2$, wherein
k is serine, threonine or diaminopropionic acid;
m is threonine, alanine or methylalanine;
n is glutamine or arginine;
q is methionine or norleucine;
u is threonine or isoleucine;
o is glycine or serine;
p is glycine, alanine, proline or N-methylglycine;
r is isoleucine, alanine or phenylglycine;
s is valine or phenylglycine;
t is phenylalanine, tryptophan, pyroglutamic acid or an amino acid with a side chain containing CH$_2$—Ar or CH$_2$—S—CH$_2$—Ar, where Ar represents phenyl or naphthyl, optionally substituted by halogen, methyl or nitro group; X is as described above, and the chain of amino acids kRmHnHSqEuRTPDINPAWYmoRp (SEQ ID NO: 35) is optionally shortened by eliminating from 1 to 11 amino acids from that portion of the chain. In some embodiments, the amino acids are not eliminated from the other portions of the chain to retain maximum binding affinity.

Yet further embodiments include a method of preventing or treating a subject diagnosed with or susceptible to having disorders characterized by an increased level of glucose in blood, comprising the step of administering to the subject of treatment the lipidated analogs of prolactin-releasing peptide having a general formula:

(Formula 2; SEQ ID NO: 2)
(X)kRmHnHSqEuRTPDINPAWYmoRprRPsGRt-NH$_2$, wherein
k, m, n, q, u, o, p, r, s, t and X are as described earlier; and the chain of amino acids kRmHnHSqEuRTPDIN-PAWYmoRp (SEQ ID NO: 35) is optionally shortened from N-terminus by eliminating from 1 to 10 amino acids.

Additional embodiments disclosed herein relate to a method of preventing or treating a subject diagnosed with or susceptible to having disorders characterized by an increased level of glucose in blood, comprising the step of administering to the subject of treatment the lipidated analogs of prolactin-releasing peptide chosen from the group containing peptides of formula:

(Formula 2; SEQ ID NO: 2)
(X)kRmHnHSqEuRTPDINPAWYmoRprRPsGRt-NH$_2$,
and (Formula 3; SEQ ID NO: 3)
(X)TPDINRAWYmoRprRPsGRt-NH$_2$, wherein
k, m, n, q, u, o, p, r, s, t and X are as described earlier.

In some embodiments, the methods include administering lipidated analogs of prolactin-releasing peptide which have substitutions of amino acids in positions 1-24 of formula 2, and/or in positions 1-13 of formula 3, that do not increase the binding affinity value of the resulting lipidated analog of prolactin releasing peptide (PrRP) to the receptor GPR10 over Ki $10^{-6}$ mol·l$^{-1}$. The binding affinities were assessed in the rat hypophyseal cell line RC-4B/C, or in CHO cells with transfected GPR10 receptor grown on 24-well plates, which had their bottom coated with polyethyleneimine, up to the optimal density of 300-450 thousand cells per well. The following agents were subsequently added: binding buffer containing 20 mmol·l$^{-1}$ HEPES, pH 7.4, 118 mmol·l$^{-1}$ NaCl, 4.7 mmol·l$^{-1}$ KCl, 5 mmol·l$^{-1}$ MgCl$_2$, 5.5 mmol·l$^{-1}$ glucose, 1 mg/ml bovine serum albumin, 0.1 mg/ml bovine pancreatic trypsin inhibitor; unlabeled analogs of PrRP at a final concentration between $10^{-11}$ to $10^{-4}$ mol·l$^{-1}$, and $^{125}$I-PrRP31 of final concentration of $10^{-10}$ mol·l$^{-1}$. The plate was incubated for 60 min at room temperature and thereafter the cells were solubilized in 0.1 mol/l solution of NaOH and the radioactivity bound to the cell was counted in a γ-counter.

Additional embodiments relate to methods comprising administering to the subject of treatment the lipidated analogs of prolactin-releasing peptide of formula:

(X)SRmHnHSqEuRTPDINPAWYmoRprRPsGRt-NH$_2$ (Formula 4; SEQ ID NO: 4), wherein m, n, q, u, o, p, r, s, t are as described earlier;

X=X$^1$ or X$^2$X$^1$, X$^1$ being C8-C18 fatty acid, preferably C10-C16 fatty acid, which is bound in one random position to an original amino acid or to a replaced amino acid of the above mentioned peptide chain directly by an amide bond or through X$^2$ which is as described earlier. In some embodiments, the lipidated analogs of prolactin-releasing peptide described herein have terminal amino acids chosen from histidine, benzylhistidine, naphthylalanine, tryptophan, pyroglutamic acid, benzylcysteine, benzyl-O-glutamate, norleucine, dichlorophenylalanine, tetrachlorophynylalanine, pentafluorophenylalanine, methyl-O-phenylalanine, methyl-NH-phenylalanine or nitrophenyalanine. In some embodiments, the method is characterized by the step of administering to the subject of treatment the lipidated analogs of prolactin-releasing peptide described herein, having the fatty acid selected from the group consisting of fatty acids with 8 to 18 carbons, preferably with 10 to 18 carbon atoms and even more preferably from 12 to 16 carbon atoms.

In some embodiments, the fatty acid has 8, 9, 10, 11, 112, 13, 14, 15, 16, 17, or 18 carbon atoms.

Further embodiments use lipidated analogs of prolactin-releasing peptide selected from the group consisting of:

(Formula 5; SEQ ID NO: 5)
(X) TPDINPAWYmoRGrRPsGRF-NH$_2$;

(Formula 6; SEQ ID NO: 6)
(X) TPDINPAWYmoRGrRPsGR 1-Nal-NH$_2$;
and (Formula 7; SEQ ID NO: 7)
(X) RmHnHSNleETRTPDINPAWYmoRGrRPsGR 1-Nal-NH$_2$;

where m, n, o, r, s and X are as described earlier, and 1-Nal is naphthylalanine.

In some embodiments, the methods described herein utilize lipidated analogs of prolactin-releasing peptide selected from:

(Formula 8; SEQ ID NO: 8)
(X) SRTHRHSMEIRTPDINPAWYASRGIRPVGRF-NH$_2$;
and (Formula 9; SEQ ID NO: 9)
(X) SRAHQHSMETRTPDINPAWYTGRGIRPVGRF-NH$_2$;

where X is as described earlier.

In some embodiments, the methods described herein use lipidated analogs of prolactin-releasing peptide according to the formula:

(Formula 11; SEQ ID NO: 11)
(X) TPDINPAWYmoRGIRPVGRF-NH$_2$ wherein in is threonine or alanine; and o is glycine or serine; and X is as described earlier.

In other embodiments, the methods described herein use lipidated analogs of prolactin-releasing peptide according to the formula:

(Formula 10; SEQ ID NO: 10)
(X) TPDINPAWYASRGIRPVGRF-NH$_2$;
or (Formula 8; SEQ ID NO: 8)
(X) SRTHRHSMEIRTPDINPAWYASRGIRPVGRF-NH$_2$, wherein X=X$^1$ or X$^1$X$^2$, X$^1$ being C12 to C16 fatty acid, which is bound in one random position to the original amino acid or to the replaced amino acid of the above mentioned peptide chain directly by the amide bond or through X$^2$, which is chosen from the group consisting of β-alanine, γ-amino butyric acid and γ-glutamic acid.

In some embodiments, the methods described herein utilize lipidated analogs of prolactin-releasing peptide according to the formula:

(Formula 10; SEQ ID NO: 10)
(X) TPDINRAWYASRGIRPVGRF-NH$_2$;
or (Formula 8; SEQ ID NO: 8)
(X) SRTHRHSMEIRTPDINPAWYASRGIRPVGRF-NH$_2$;

wherein X=X$^1$ or X$^1$X$^2$, X$^1$ being myristic or palmitic acid, which is bound to an original or replaced amino acid of formula 10 or formula 8, directly by an amide bond or through X$^2$, which is selected from the group consisting of polyoxyethylene, β-alanine, γ-amino butyric acid and γ-glutamic acid.

In some embodiments, the methods described herein utilize lipidated analogs of prolactin releasing peptide, In other embodiments, the lipidated analogs of prolactin-releasing peptide utilized are according to the formula:

(Formula 10; SEQ ID NO: 10)
(X) TPDINPAWYASRGIRPVGRF-NH$_2$;
or (Formula 8; SEQ ID NO: 8)
(X) SRTHRHSMEIRTPDINPAWYASRGIRPVGRF-NH$_2$;

wherein X=X$^1$ or X$^1$X$^2$, X$^1$ being myristic or palmitic acid, which is bound to an original or replaced amino acid of formula 10 or formula 8, directly by an amide bond or through X$^2$, which is γ-glutamic acid.

In some embodiments, lipidated analogs of prolactin-releasing peptide used in methods described herein are according to the formula:

(Formula 10; SEQ ID NO: 10)
(X) TPDINPAWYASRGIRPVGRF-NH$_2$
or (Formula 8; SEQ ID NO: 8)
(X) SRTHRHSMEIRTPDINPAWYASRGIRPVGRF-NH$_2$, wherein X=X$^1$ or X$^2$X$^1$, X$^1$ being myristic or palmitic acid, which is bound to original or replaced amino acid 1, 11 or 18 of formula 8, or 1, 5 or 7 of formula 10, either directly by an amide bond or through X$^2$, which is γ-glutamic acid.

In some embodiments, the methods described herein use lipidated analogs of prolactin-releasing peptide according to the formula:

(Formula 10; SEQ ID NO: 10)
(X) TPDINPAWYASRGIRPVGRF-NH$_2$
or (Formula 8; SEQ ID NO: 8)
(X)SRTHRHSMEIRTPDINPAWYASRGIRPVGRF-NH₂, wherein X=X¹ or X²X¹, X¹ being myristic or palmitic acid, which is bound original replaced amino acid 1 or 11 of formula 8, or 1 or 7 of formula 10, directly by an amide bond or through X², which is γ-glutamic acid.

Some embodiments described herein relate to a method of preventing or treating a subject diagnosed with or susceptible to having a disorders characterized by an increased level of glucose in blood comprising the step of administering to the subject of treatment the lipidated analogs of prolactin-releasing peptide according to the formula:

(SEQ ID NO: 12)
SRTHRHSMEIK(palm)TPDINPAWYASRGIRPVGRF-NH₂;

(SEQ ID NO: 13)
TPDINPK(palm)WYASRGIRPVGRF-NH₂;

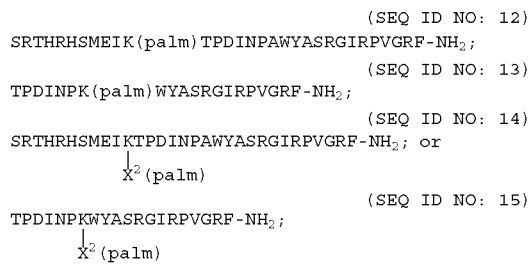

(SEQ ID NO: 14)
SRTHRHSMEIKTPDINPAWYASRGIRPVGRF-NH₂; or
         |
         X²(palm)

(SEQ ID NO: 15)
TPDINPKWYASRGIRPVGRF-NH₂;
      |
      X²(palm)

where palm is palmitic acid and X² is γ-glutamic acid or polyoxyethylene.

In some embodiments, X² is linked to K.

Additional embodiments relate to a method of preventing or treating disorders is characterized by an increased level of glucose in blood comprising the step of administering to the subject at least one lipidated analog of prolactin-releasing peptide selected from the group consisting of:

(SEQ ID NO: 16)
X¹-SRAHQHSMETRTPDINPAWYTGRGIRPVGRF-NH₂;

(SEQ ID NO: 17)
X¹-SRTHRHSMEIRTPDINPAWYASRGIRPVGRF-NH₂;

(SEQ ID NO: 18)
(N-palm)-SRTHRHSMEIRTPDINPAWYASRGIRPVGRF-NHMe;

(SEQ ID NO: 19)
(N-palm)-SRTHRHSMEIRTPDINPAWYASRGIRPVGRF-NOMe;

(SEQ ID NO: 20)
(N-myr)-TPDINPAWYTGRGIRPVGRF-NH₂;

(SEQ ID NO: 21)
(N-myr)-TPDINPAWYASRGIRPVGRF-NH₂;

(SEQ ID NO: 22)
(N-oct)-TPDINPAWYASRGIRPVGRF-NH₂;

(SEQ ID NO: 23)
(N-dec)-TPDINPAWYASRGIRPVGRF-NH₂;

(SEQ ID NO: 24)
(N-dodec)-TPDINPAWYASRGIRPVGRF-NH₂;

(SEQ ID NO: 25)
X¹'-SRAHQHS Nle ETRTPDINPAWYTGRGIRPVGRF-NH₂;

(SEQ ID NO: 26)
X¹-SRAHQHS Nle ETRTPDINPAWYTGRGIRPVGR 1-Nal-NH₂;

(SEQ ID NO: 27)
X¹-SRAHQHS Nle ETRTPDINPAWYTGRGIRPVGR PheCl2-NH₂;

(SEQ ID NO: 28)
X¹-SRAHQHS Nle ETRTPDINPAWYTGRGIRPVGR PheNO2-NH₂;

(SEQ ID NO: 29)
X¹-SRAHQHS Nle ETRTPDINPAWYTGRGIRPVGR PheF5-NH₂;

(SEQ ID NO: 30)
X¹-SRAHQHS Nle ETRTPDINPAWYTGRGIRPVGRY-NH₂;

(SEQ ID NO: 31)
X¹-SRAHRHS Nle EIRTPDINPAWYASRGIRPVGRY-NH₂;

(SEQ ID NO: 32)
(N-myr)-Nle-ETRTPDINPAWYTGRGIRPVGRF-NH₂;

(SEQ ID NO: 33)
(N-myr)-QHSMETRTPDINPAWYTGRGIRPVGRF-NH₂;
and (SEQ ID NO: 34)
(N-myr)-QHSMETRTPDINPAWYASRGIRPVGRF-NH₂;

wherein X¹ is palmitic acid, myristic acid or stearic acid; and

X¹ is palmitic acid or myristic acid.

Pharmaceutical Compositions, Routes of Administration and Dosing

Described herein, in certain embodiments, are pharmaceutical compositions comprising at least one lipidated analog as described herein and methods of treatment using these pharmaceutical compositions.

Pharmaceutical compositions are typically formulated using one or more physiologically acceptable carriers, including excipients and auxiliaries, which facilitate processing of the therapeutic composition into preparations which are used pharmaceutically. Proper formulation is dependent upon the route of administration chosen, storage conditions and other factors known in the art. A summary of pharmaceutical compositions is found, for example, in Remington: The Science and Practice of Pharmacy, Nineteenth Ed (Easton, Pa.; Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins, 1999). Pharmaceutically acceptable excipients and dosage forms may be prepared as is known it the art.

Described herein are pharmaceutical compositions that include one or more lipidated analogs described herein, and one or more pharmaceutically acceptable diluent(s), excipient(s), or carrier(s). In addition, the lipidated analog is optionally administered as pharmaceutical compositions in which it is mixed with other active ingredients, as in combination therapy. In some embodiments, the pharmaceutical compositions include using a pharmaceutically acceptable salt, amide, or ester of the selected lipidated analog. In some embodiments, the pharmaceutical composition includes other medicinal or pharmaceutical agents, carriers, adjuvants, such as preserving, stabilizing, wetting or emulsifying agents, solution promoters, salts for regulating osmotic pressure, and/or buffers. In addition, the pharmaceutical compositions can also contain other therapeutically valuable substances.

A pharmaceutical composition, as used herein, refers to a mixture of a lipidated analog with one or more other chemical components, such as carriers, stabilizers, diluents, dispersing agents, suspending agents, thickening agents, and/or excipients. The pharmaceutical composition facilitates administration of the lipidated analog to an organism. In practicing the methods of treatment or use provided herein, a lipidated analog is administered in a pharmaceutical composition to a mammal having a condition, disease, or disorder to be treated. Preferably, the mammal is a human. The dose and dosing regimen varies depending on the severity and stage of the condition, the age and relative health of an individual, the potency of the therapeutic composition used and other factors. The lipidated analog is optionally used singly or in combination with one or more therapeutic agents as components of mixtures.

In some embodiments, the pharmaceutical compositions described herein can be formulated, for example, as aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations. The pharmaceutical formulations described herein are optionally administered to an individual by one or more administration routes, including but not limited to, parenteral (e.g., intravenous, subcutaneous, intramuscular, intrathecal), intracerebroventricular, intranasal, buccal, topical, rectal, oral, or transdermal administration routes. In some embodiments, lipidated analogs are administered by subcutaneous injection or intravenous routes.

In some embodiments, an individual is administered a therapeutically effective amount of one or more lipidated analogs, as well as suitable excipients. In some embodiments, the lipidated analogs are administered for medical treatments relating to lowering of higher glucose level in blood. In some embodiments, the lipidated analogs are administered for prevention and/or treatment of all forms of diabetes and related diseases, such as eating disorders and/or diabetic complications.

In some embodiments, the lipidated analogs are administered for delaying or preventing diabetic disease progression as for example progression of impaired glucose tolerance.

In some embodiments, lipidated analogs are combined with one or more additional pharmacologically active substances, such as antidiabetic agents, antiobesity agents, antihypertensive agents, appetite regulating agents, and other know agents for the treatment and/or prevention of complications resulting from or associated with higher glucose level in blood or diabetes or obesity.

In some embodiments, lipidated analogs are combined with surgery or other procedure that influences the glucose level in blood and/or lipid homeostasis, such as gastric banding or gastric bypass.

EXAMPLES

The following specific, non-limiting examples are to be construed as merely illustrative, and do not limit the present disclosure of the scope of the invention. Without further elaboration, it is believed that one skilled in the art can, based on the description herein, utilize the present disclosure to its fullest extent. Exemplary results from the experiments are presented in FIGS. 1-5 and in Table 2-4 below.

The following abbreviations are used herein: analysis of variance (ANOVA); bovine serum albumin (BSA); bovine pancreatic trypsin inhibitor (BPTI); epidermal growth factor (EGF); 4-(2-hydroxyethyl)-1-piperazineethansulfonic acid (HEPES); phosphate buffer saline (PBS); sodium dodecyl sulfate (SDS); Tris-buffered saline (TBS); diaminopropionic acid (Dpr); 1-naphthylalanine (1-Nal); norleucine (Nle); myristoyl (myr); palmitoyl (palm); octanoyl (oct); dodecanoyl (dodec); and tridecanoyl (tridec); γ-aminobutyric acid (GABA), gamma-glutamic acid (γE), polyoxyethylene (POE), particularly 1,13-diamino-4,7,10-trioxatridecan-succinamic acid.

Example 1: Synthesis of Lipidated PrRP Peptides and Lipidated PrRP Analogs

The peptides described in this disclosure (e.g, peptides described in Table 1) were synthesized using the solid phase synthesis method according to Maixnerová et al. (Maixnerová, J., et al., "Structure activity relationship of CART (cocaine- and amphetamine-regulated transcript) peptide fragments," Peptides, 28:1945-1953, 2007), utilizing the Fmoc strategy on an ABI 433A synthesizer (Applied Biosystems, Foster City, Calif., USA). Lipidation of the peptide with the appropriate fatty acid was performed before cleaving the peptide off the resin as described in Maletínská, L., et al., "Characterization of new stable ghrelin analogs with prolonged orexigenic potency," J Pharmacol Exp Ther, 340:781-786, 2012.

The labeled peptide PrRP31 used in the competitive binding experiments was iodinated with Na125I using Iodo-Gen (Pierce, Rockford, Ill., USA) according to the published procedure (Maixnerová et al., 2011). Monoiodinated peptides were stored in aliquots at −20° C., and used in binding assays within one month.

Example 2: Competitive Binding Experiments

Competitive binding experiments were performed according to Motulsky and Neubig (Motulsky, A., et al., "Analyzing radioligand binding data," *Curr Protoc Neurosci*, Chapter 7, Unit 7.5, 2002). Binding experiments were conducted with rat pituitary cells, and with Chinese Hamster Ovary (CHO) cells as follows:

The rat pituitary cell line RC-4B/C (ATCC, Manassas, USA) was grown on 24-well plates which had their bottom coated with polyethyleneimine. The cells were grown to the optimal density of 300-450 thousand cells per well. The following agents were used for the experiment: binding buffer (20 mmol·l$^{-1}$ HEPES, Ph 7.4; 118 mmol·l$^{-1}$ NaCl, 4.7 mmol·l$^{-1}$ KCl, 5 mmol·l$^{-1}$ MgCl$_2$, 5.5 mmol·l$^{-1}$ glucose, 1 mg/ml BSA, 0.1 BPTI), unlabeled analogs of PrRP (i.e. the analog being tested) at a final concentration between $10^{-11}$ to $10^{-4}$ mol·l$^{-1}$, and rat $^{125}$I-PrRP31 (labeled with radioactive Iodine-125) at a final concentration of $10^{-1}$ mol·l$^{-1}$ (Maixnerová et al., 2011).

CHO cells transfected with human PrRP receptor GPR10 (Perkin Elmer, USA) were grown on 24-well plates coated with polyethyleneimine. The cells were grown to the optimal density of 40-80 thousand cells per well. The following agents were used for the experiment: binding buffer (25 mmol·l$^{-1}$ Tris, pH 7.4; 118 mmol·l$^{-1}$ NaCl, 10 mmol·l$^{-1}$ MgCl$_2$, 10 mmol·l$^{-1}$ CaCl$_2$, 5.5 mmol·l$^{-1}$ glucose, 0.5 mg/ml BSA), unlabeled analogs of PrRP (i.e. the analog being tested) at a final concentration between $10^{-11}$ to $10^{-4}$ mol·l$^{-1}$, and radiolabeled human $^{125}$I-PrRP31 at a final concentration of $5\times10^{-11}$ mol·l$^{-1}$.

Plates were incubated for 60 minutes at room temperature. After incubation, the cells were solubilized in 0.1 mol/l solution of NaOH, and the radioactivity bound to the cells was counted using a γ-counter. The experiments were performed in duplicate, and repeated at least three times.

Nearly all the tested rat and human PrRP analogs (for structures, see Table 1), including the lipidated analog of prolactin releasing peptide (PrRP)s, bound to the rat receptor with high affinity in RC-4B/C cells (Table 2), and also to the human receptor GPR10 in CHO cells (Table 2). Generally, as the length of the fatty acid chain increased, the value of $K_i$ decreased, indicating that the affinity was stronger with the lipidated PrRP analogs. Binding affinity of lipidated analogs were up to an order of magnitude stronger as compared to the original unlipidated analog of prolactin releasing peptide (PrRP) (see Table 2).

The results indicated that lipidation of the tested peptides led to an increase in receptor binding, and that lipidation of the peptides lowered the $K_i$ value, or resulted in increased binding affinity, in both rat RC-4B/C cell receptor and human GPR10 receptor. The increased binding affinity correlated with increasing chain length of the fatty acid present on the lipidated analog. The addition of fatty acid not only preserved receptor binding (as a result of N-terminal lipidation, whereas the receptor binding depends on the C-terminal RF-amide), it actually increased the binding affinity by up to an order of magnitude.

Human lipidated PrRP analogs (see Table 1, analog nos. 2, 39, 40, 41, 43) displaced to a similar extent the binding of both the rat and human $^{125}$I-PrRP in the RC-4B/C cells to the rat PrRP receptor, and to human GPR10 receptor, in the nmol·l$^{-1}$ range (see Table 2). Lipidized shortened PrRP31 analogs (21-30 amino acids) showed binding affinities similar to both native forms of PrRP. Scrambled peptides, (analog nos. 19, 20, 25, 26), in contrast, showed very low binding affinity (high $K_i$) and no effect on food intake in mice (Table 2).

Graph Pad Prism Software (San Diego, Calif., USA) was used for evaluating the competitive binding experiments. Nonlinear regression was performed using a onsite binding model. The $K_i$ values were calculated using the Cheng and Prussof equation (Cheng, Y., et al., "Relationship between the inhibition constant ($K_i$) and the concentration of inhibitor which causes 50 percent inhibition (IC50) of an enzymatic reaction," *Biochem Pharmacol,* 22:33099-3108, 1973), using A $K_d$ value of 4.21 nmol·l$^{-1}$ and a radioligand concentration of 0.1 nmol·l$^{-1}$ (Maixnerová et al., 2011).

Example 3: Cellular Signaling

Experiments were also conducted to determine if the various lipidated PrRP20 analogs initiated the MAPK/ERK1/2 signaling pathway. PrRP31, which is known to initiate MAPK/ERK1/2 signaling, was used for comparison.

RC-4B/C cells were grown in 6-well plates up to the optimal density of 700-900 cells per well. Seventeen hours prior to sample harvest, the growth medium was replaced by a serum-free medium lacking epidermal growth factor (EGF). The lipidated PrRP20 analogs being tested were added to each well at a final concentration of $10^{-6}$ mol·l$^{-1}$. After a 5 minute incubation at 37° C., the plate was placed on ice and each well was rinsed three times with PBS pH 7.4 (137 mmol·l$^{-1}$ NaCl, 2.7 mmol·l$^{-1}$ KCl, 8 mmol.$^{-1 \cdot -1}$ $N_{a2}HPO_4 \cdot 2H_2O$ and 1.76 mmol·l$^{-1}$ $K_{H2}PO_4$) and cooled to 4° C. The cells were then solubilized in a sample buffer (62.5 mmol.$^{-1 \cdot -1}$ Tris-HCl Ph 6.8, 10% glycerol, 2% SDS, 0.01% bromophenol blue, 5% merkaptoethanol, 50 mmol.$^{1 \cdot -1}$ NaF and 1 mmol.$^{1 \cdot -1}$ $Na_3VO_4$), and collected into microtubes and frozen at −20° C. Samples were collected in at least three independent experiments.

Western blot analysis was used to determine if the lipidated PrRP20 analogs initiated the MAPK/ERK1/2 signaling pathway. Electrophoresis was performed on 5%/12% polyacrylamide gel in the presence of SDS (SDS-PAGE) on the instrument MiniProtean 3 (BioRad, Hercules, Calif., USA). Samples that were loaded on the gel were first disintegrated by ultrasound, then heated at 100° C. for 2 minutes, and centrifuged for 5 minutes at 500×g at room temperature. PrRP31, which was shown to initiate MAPK/ERK1/2 signaling (Maixnerová et al., 2011), was used as a positive control. Electrophoresis was performed at a constant voltage of 100 V for 10 minutes, or for 60 minutes at 150 V.

To show the presence of phosphorylated proteins in the samples, the proteins from the SDS-PAGE gel were transferred to the Immobilon™-P PVDF (polyvinylidene difluoride) membrane (Sigma-Aldrich, USA). The transfer was performed in blotting buffer at pH 8.3 (25 mmol·l$^{-1}$ Tris, 192 mmol·l$^{-1}$ glycine and 20% methanol) for 20 hours at 4° C. at a constant voltage of 30 V.

After the transfer of protein to the PVDF membrane, the membranes were washed for 5 minutes in TBS washing buffer (20 mmol·l$^{-1}$ Tris, 140 mmol·l$^{-1}$ NaCl and 0.1% Tween-20) and then incubated for 1 hour in blocking buffer (TBS with 5% non-fat milk powder and 5 mmol·l$^{-1}$ $Na_3VO_4$ and 50 mmol·l$^{-1}$ NaF) at room temperature. Further, the membranes were washed three times for 5 minutes using the TBS washing buffer. The membranes were then incubated with the primary antibody against phospho-p44/42 MAPK (Thr202/Tyr204) (Cell Signaling Technology, Beverly, USA) which was diluted in blocking buffer at 1:1000. After three washes with the TBS washing buffer for 5 minutes, the membranes were incubated for 1 hour with rabbit secondary antibody labeled with peroxidase (Sigma, St. Louis, USA), which was diluted in blocking buffer at 1:12,000. The membranes were then washed three times in TBS washing buffer for 5 minutes and the solution Femto (Pierce SuperSignal, Thermo Fisher Scientific, Rockford, Ill., USA) was subsequently applied. The induced chemiluminiscence was detected by a CCD camera (LAS 3000, Fuji Photo Film GmBH, Düsseldorf, Germany).

To assess the level of phosphorylation, a densitometric analysis using the program Quantity One (BioRad, Hercules, Calif., USA) was used. One-way ANOVA with subsequent Dunnett post-hoc test was used to determine the statistical significance of the densitometric analysis. Data was found to be statistically significant with a P-value<0.05.

All peptides with high affinity (indicated by relatively low $K_i$ values) to GPR10 receptor were found to be agonists. The values of the inhibition constant K were calculated from $IC_{50}$ using Cheng and Prusoff's equation, using a $K_d$ value 4.21 nmol.$^{1 \cdot -1}$±S.E.M. found in the saturation binding experiments, and radioligand concentration of 0.1 nmol·l$^{-1}$.

Example 4: In Vivo Tests

The food intake test and glucose tolerance test (GTT) was performed to show the in vivo effects of PrRP20, PrRP31, and their lipidated analogs on the appetite and blood glucose levels as well as other metabolic parameters of rats and mice. The results are summarized in FIGS. 1-5, in the "Food intake in mice" column of Table 2, and Tables 3-4.

NMRI mice, C57BL/6 mice, and Wistar rats (AnLab, Prague, Czech Republic) were housed in a temperature of 23° C. and a daily cycle of 12 h light and dark (light from 6:00). They were given ad libitum water and a standard chow diet that contained 25, 9 and 66% of calories of protein, fat and carbohydrate respectively. Energy content of the feed was 3.4 kcal/g (St-1, Mlýn Kocanda, Czech Republic). Db/db mice and their controls (C57BL/6 background) were obtained from Taconic (Denmark), housed under the same conditions as described above, and fed by Altromin (Taconic, Denmark). ZDF-Lepr$^{fa}$/Crl, diabetic fa/fa male rats were obtained from Charles River (France), housed under same conditions as described above, and fed with a Purina 5008 diet (IPS Product Supplies Limited, UK). All experiments followed the ethical guidelines for animal experiments and the law of the Czech Republic Nr. 246/1992.

a) Food Intake Experiments

In experiments with C57BL/6 mice or Wistar rats, food intake was measured with overnight fasted animals in individual cages. Food was withdrawn 17 hours prior to injection of lipidated analog of prolactin releasing peptide (PrRP); free access to water was maintained. The administration of either saline, PrRP, or lipidated analogs was performed by SC injection at doses of 1-10 mg/kg (which corresponded to a volume of 0.2 ml/mouse and 0.1 ml/100 g weight of rat). Fifteen minutes after the lipidated analog of prolactin releasing peptide (PrRP) administration, the mice were given pre-weighed food. The food was then weighed every 30 minutes for 5-10 hours. The administration of each dose was performed at least twice, and each group of mice consisted of at least 6 mice. The results were evaluated as % of food intake relative to the control group injected with saline, as shown in Table 2. Food intake was reduced for most mice given non-scrambled lipidated analog of prolactin releasing peptide (PrRP)s compared to controls given unlipidated PrRP, and in many cases drastically reduced. Food intake was significantly reduced in rats given peptides 43, 48, 52, 53, 54, 55 or 57 compared to controls given vehicle.

b) Effect of Administration of Analog 43 in Lean Mice on Blood Glucose

Intraperitoneal glucose tolerance test (IPGTT) was performed in overnight fasted male C57BL/6 mice (AnLab, Praha, Czech Republic) at age of 12 weeks. Initial blood (from tail vein) glucose levels were measured, and afterwards either analog 43 (5 mg/kg SC) or saline were administered to the mice (n=7). 15 min later, 2 g/kg glucose solution was administered IP. Blood glucose was then measured at 15, 30, 60, 120 min from glucose injection using a glucometer (Glucocard, Arkray, Kyoto, Japan).

Figure 1B:
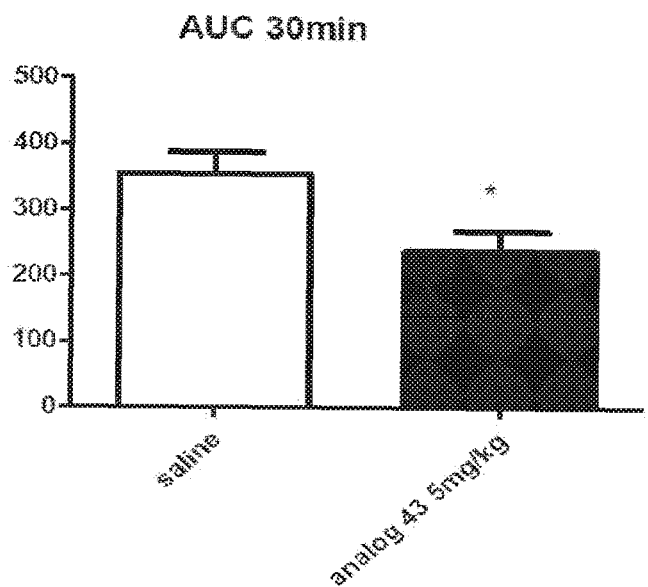

FIGS. 1A and 1B show the results of the IPGTT tests after acute administration of palm-PrRP31 (analog 43) and of control saline in lean mice. IPGTT was performed in overnight fasted male C57BL/6 mice, Blood glucose levels were measured at the beginning and after subcutaneous (SC—beneath the skin) administration of palm-PrRP31 (5 mg/kg SC) or saline (n=7) at time 30, 60, 90 and 120 min post injection. FIG. 1A shows glucose levels over time, while FIG. 1B shows Area Under Curve (AUC) through time of 30 min. Regarding the error bars in the graphs *P<0.05, **P<0.01. IPGTT glucose levels were lower in mice given analog 43 instead of saline, particularly early in the experiment. Total area under the curve was also clearly lower in analog 43 mice.

c) Effect of 10 Days Repeated Administration of Analog 43 to Obese Diabetic Monosodium-Glutamate (MSG) Mice on Blood Glucose Obese mice were created using MSG. L-glutamic acid sodium salt hydrate (Sigma, St. Louis, USA) was subcutaneously (SC) administered to newborn male mice, at a dose of 4 mg/g body weight, daily from postnatal days 2 to 8 to induce obesity. The MSG treated mice used for experiments were 24 weeks old. Age related mice were used as controls. Obese and control mice were placed into separate cages with free access to food and water. The following week, mice were subjected to a 10-day food intake experiment. MSG mice were SC injected with saline or analog 43 at dose of 5 mg/kg and their NMRI controls were injected with saline (n=10) twice a day for ten days. Consumption of the St-1 diet and the body weight of the mice were simultaneously followed. After 10 days of treatment, mice were fasted overnight and IPGTT was performed. After initial blood glucose measurement, 2 g/kg glucose solution was administered IP.

Blood glucose was then measured at 15, 30, 60, 120 and 180 min post injection as described above.

Figure 2A:
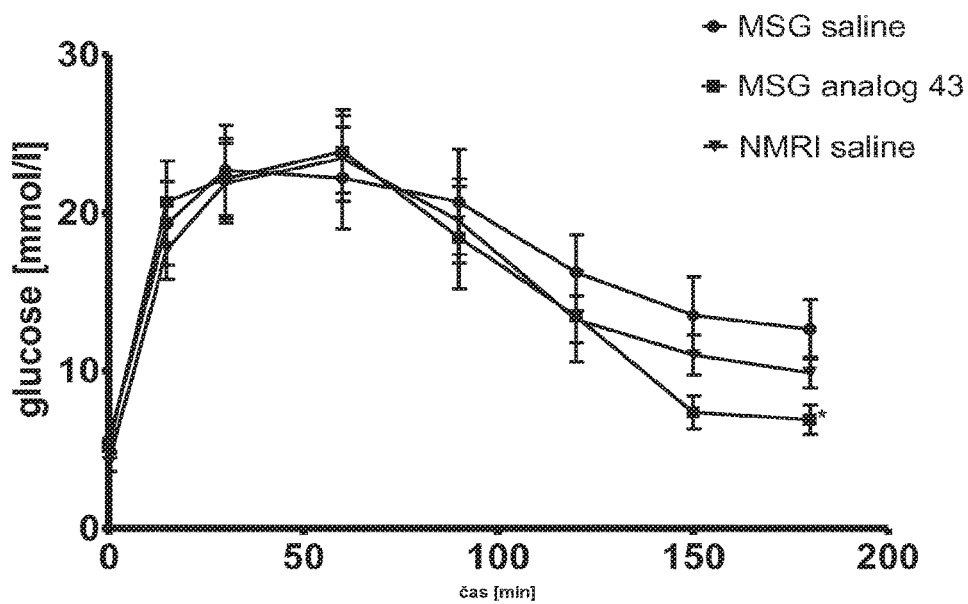
FIGS. 2A and 2B illustrate intraperitoneal glucose tolerance test (IPGTT) results after 10 days of administration of palm-PrRP31 (analog 43) to obese diabetic monosodium-glutamate (MSG) mice. Mice were subjected to a 10-day food intake experiment. MSG mice were SC injected with either saline or palm-PrRP31 (analog 43) at a dose of 5 mg/kg, and their NMRI controls with saline (n=10), twice a day for ten days. After 10 days of treatment, mice were fasted overnight and IPGTT was performed. After initial blood glucose measurement, 2 g/kg glucose solution was administered intraperitoneally (IP). Blood glucose was then measured at 15, 30, 60, 120 and 180 min.
Figure 2B:
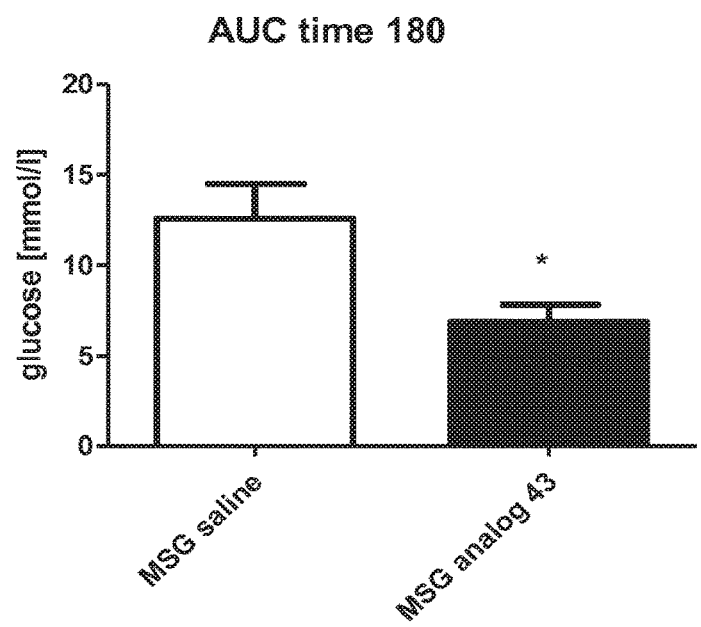

FIGS. 2A and 2B represent IPGTT results after 10 days of administration of palm-PrRP31 (analog 43) to the obese MSG and control NMRI mice. FIG. 2A shows resulting glucose levels over time, and FIG. 2B compares Area Under Curve (AUC) through 180 min. IPGTT blood glucose levels were lower in the mice given analog 43 than those administered saline, particularly later in the trial after the initial blood glucose peak was reached. Area under the curve was also substantially lower in mice receiving analog 43.

d) Effect of 14 Days Repeated Administration of Analog 43 to Diabetic Db/Db Mice on Blood Glucose Db/db male mice and their respective controls were acclimatized after arrival, housed 2-3 mice per cage, and used in the experiment at age 11-12 weeks. Mice had free access to food and water, and were subjected to a 14-day experiment. Db/db mice were SC injected with either analog 43 at a dose of 5 mg/kg, or with control saline (n=10) twice a day for 14 days. The body weight of the mice was followed simultaneously. Following 14 days of treatment, mice were fasted overnight and IPGTT was performed. After initial blood glucose measurement, 2 g/kg glucose solution was administered IP, and glucose levels were measured every hour for 7 hours.

Figure 3:
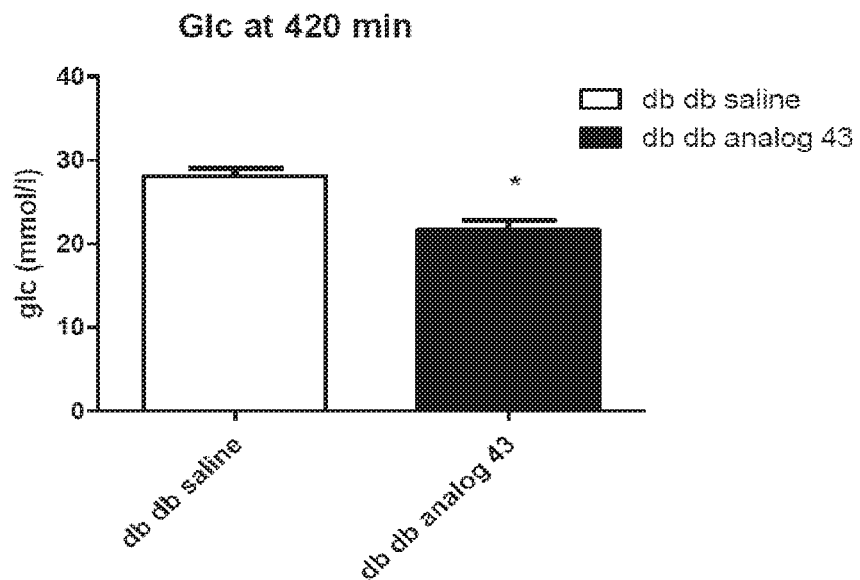
FIG. 3 illustrates a comparison of glucose levels after 14 days of repeated administration of palm-PrRP31 (analog 43) or saline, as a control, to diabetic db/db mice. Db/db male mice were SC injected with saline or palm-PrRP31 (analog 43) at dose of 5 mg/kg twice a day for 14 days. Then, mice were fasted overnight and IPGTT was performed. After initial blood glucose measurement, 2 g/kg glucose solution was administered IP and glucose followed every hour for 7 hours. Glucose level is shown at the end of the experiment (420 min).

FIG. 3 compares IPGTT glucose levels after 14 days of repeated administration of palm-PrRP31 (analog 43) vs. saline to diabetic db/db mice. Glucose levels are shown for the end of the experiment (420 min), and are significantly lower in the diabetic mice where analog 43 were administered.

e) Effect of Acute Administration of Analog 43 in Lean Rats on Blood Glucose

IPGTT was performed in overnight fasted male Wistar rats (Antab, Praha, Czech Republic) at age of 14 weeks. Initial blood (from tail vein) glucose levels were measured, and subsequently either analog 43 (5 mg/kg IP) or saline were administered to mice (n=7). 15 min later, 2 g/kg glucose solution was administered IP. Blood glucose was then measured at 15, 30, 60, and 120 min from glucose injection.

Figure 4:
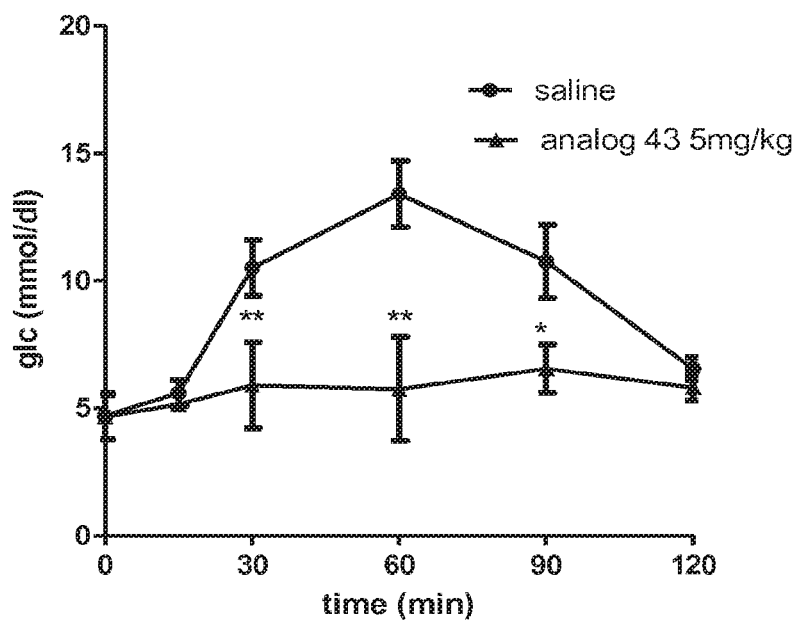
FIG. 4 illustrates a plot of glucose levels after acute administration of palm-PrRP31 (analog 43) in rats. IPGTT was performed in overnight fasted male Wistar rats. Blood glucose levels were measured at the beginning and over time after SC administration of palm-PrRP31 (analog 43) (5 mg/kg SC) or saline.

FIG. 4 illustrates a plot of glucose levels after acute administration of palm-PrRP31 in rats. IPGTT was performed in overnight fasted male Wistar rats. Blood glucose levels were measured at the beginning and over time after SC administration of palm-PrRP31 (analog 43) (5 mg/kg SC) or saline. As shown, saline rats on average experienced a large spike in blood glucose and the rats given analog 43 did not.

f) Effect of 21 Days Repeated Administration of Analog 43 and 52 in Diabetic ZDF Rats on Food Intake, Blood Glucose and Metabolic Parameters The ZDF rats were treated with vehicle or analogs 43 and 52 (1 and 5 mg/kg IP) dissolved in phosphate buffered saline, pH 6, twice daily for 21 days and sacrificed on day 22. Food intake was measured daily up to day 22. Leptin, insulin, cholesterol and HbA1c levels were measured on day 21. Glucose tolerance test (OGTT) was also performed on day 21.

Table 3 shows cumulative food intake at days 0, 7, 14 and 21. Food intake in free fed ZDF diabetic rats was significantly lowered after chronic IP treatment with analogs 43 and 52 at a dose of 5 mg/kg twice daily compared to controls treated with vehicle.

Table 4 describes metabolic parameters on day 21, at the end of experiment. Blood cholesterol levels were significantly lowered after repeated treatment with analog 43 at a dose of 1 and 5 mg/kg twice daily compared to controls.

Figure 5A:
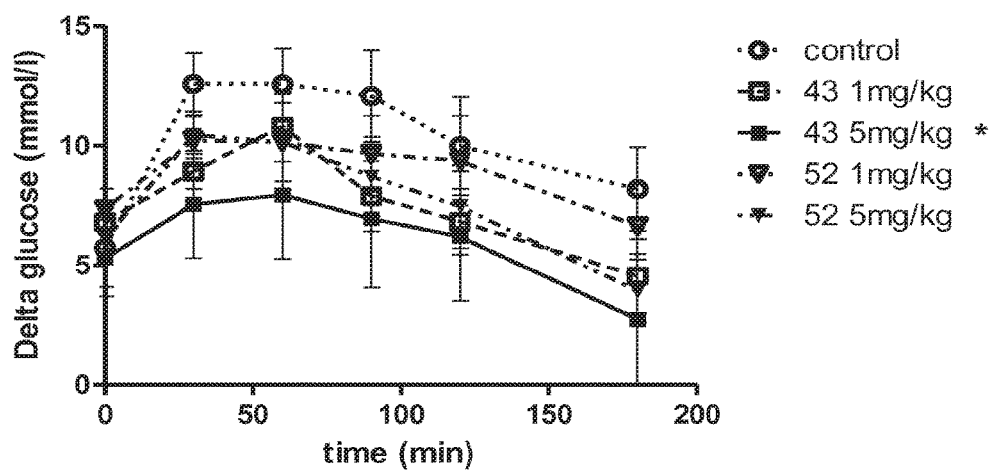
FIGS. 5A and 5B illustrate oral glucose tolerance test (OGTT) results after 21 days of administration of analog 43 and 52 to diabetic ZDF rats. Rats were subjected to a 21-day food intake experiment. ZDF rats were IP injected with either phosphate-buffered saline pH6 (control) or compound 43 or 52 at a dose of 1 and 5 mg/kg (n=8), twice a day for 21 days. After 21 days of treatment, rats were fasted overnight and OGTT was performed. After initial blood glucose measurement, 2 g/kg glucose solution was administered by oral gavage. Blood glucose was then measured at 15, 30, 60, 90, 120 and 180 min.
Figure 5B:
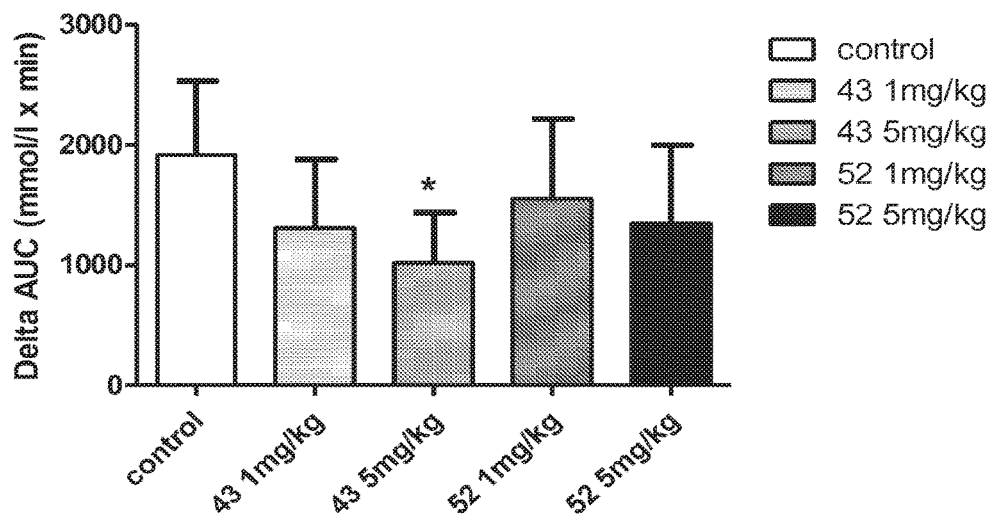

FIG. 5 shows the results for the OGTT after 21 days of administration of palm-PrRP31 (analog 43). FIG. 5A shows resulting glucose levels over time, and FIG. 5B compares Area Under Curve (AUC) through 180 min. The results indicate that repeated administration of analog 43 at a dose of 5 mg/kg twice daily caused significant lowering of the OGTT blood glucose levels. Rats were subjected to a 21-day food intake experiment. ZDF rats were IP injected with either phosphate-buffered saline pH6 (control) or compound 43 or 52 at a dose of 1 and 5 mg/kg (n=8), twice a day for 21 days. After 21 days of treatment, rats were fasted overnight and OGTT was performed. After initial blood glucose measurement, 2 g/kg glucose solution was administered by oral gavage. Blood glucose was then measured at 15, 30, 60, 90, 120 and 180 min. FIG. 5A illustrates resulting changes in glucose levels (delta glucose) over time, and FIG. 5B illustrates Area Under Curve (AUC) through 180 min. The statistical significance, denoted by the asterisk (*), was *P<0.05.

Statistical Analysis

Data are presented as means±SEM (standard error) for the number of animals indicated in the Methods and Tables. The raw data was analyzed by one-way ANOVA followed by Dunnett post hoc test using Graph-Pad Software (San Diego, Calif., USA). P<0.05 was considered statistically significant. Area under curve (AUC) was also calculated using Graph-Pad Software.

TABLE 2

Affinity to the rat receptor in RC-4B/C cells and human GPR10 receptor transfected in CHO cells, and food intake in fasted mice (45 min after SC injection).

| SEQ ID NO | Analog no. | Sequence | RC-4B/C rat pituitary cells $^{25}$I-rat PrRP31 | | GPR10 human receptor transfected in CHO cells | | Food intake in mice (5 mg/kg) % of saline-treated group |
|---|---|---|---|---|---|---|---|
| | | | $K_i$ (Nm) | % of PrRP31 | $K_i$ (Nm) | % of PrRP31 | |
| 37 | Rat PrRP20 | TPDINPAWYTGRGIRPVGRF-NH$_2$ | 3.44 ± 0.85 | 143 | 5.56 ± 0.70 | 70 | 100 |
| 38 | Human PrRP20 | TPDINPAWYASRGIRPVGRF-NH$_2$ | 1.78 ± 0.46 | 277 | 8.70 ± 1.56 | 45 | 100 |
| 39 | Rat PrRP31 | SRAHQHSMETRTPDINPAW YTGRGIRPVGRF-NH$_2$ | 4.93 ± 0.61 | 100 | 3.89 ± 1.12 | 100 | 100 |
| 40 | Human PrRP31 | SRTHRHSMEIRTPDINPAWY ASRGIRPVGRF-NH$_2$ | 2.38 ± 0.19 | 207 | 4.53 ± 0.80 | 86 | 100 |
| 41 | 1 | (myr)TPDINPAWYTGRGIRP VGRF-NH$_2$ | 0.78 ± 0.45 | 632 | 2.93 ± 0.20 | 133 | 32 |
| 42 | 2 | (myr)TPDINPAWYASRGIRP VGRF-NH$_2$ | 0.48 ± 0.18 | 1027 | 4.33 ± 0.25 | 90 | 10 |
| 43 | 3 | SRAHQHS Nle ETRTPDI NPAWYTGRGIRPVGRF-NH$_2$ | 1.28 ± 0.2 | 385 | 1.92 ± 0.43 | 203 | 100 |
| 44 | 4 | (N-oct)SRAHQHS Nle ETRTPDI NPAWYTGRGIRPVGRF-NH$_2$ | 0.98 ± 0.22 | 503 | 1.53 ± 0.07 | 254 | 94 |
| 45 | 5 | (N-dec)SRAHQHS Nle ETRTPDI NPAWYTGRGIRPVGRF-NH$_2$ | 0.65 ± 0.41 | 758 | 1.46 ± 0.57 | 266 | 57 |
| 46 | 6 | (N-dodec)SRAHQHS Nle ETRTPDI NPAWYTGRGIRPVGRF-NH$_2$ | 0.39 ± 0.14 | 1264 | 1.19 ± 0.36 | 327 | 22 |
| 47 | 7 | (N-myr)SRAHQHS Nle ETRTPDI NPAWYTGRGIRPVGRF-NH$_2$ | 0.69 ± 0.09 | 714 | 0.71 ± 0.09 | 548 | 3 |
| 48 | 8 | (N-palm)SRAHQHS Nle ETRTPDI NPAWYTGRGIRPVGRF-NH$_2$ | 0.51 ± 0.16 | 967 | 3.03 ± 0.34 | 128 | 7 |

TABLE 2-continued

Affinity to the rat receptor in RC-4B/C cells and human GPR10 receptor transfected in CHO cells, and food intake in fasted mice (45 min after SC injection).

| SEQ ID NO | Analog no. | Sequence | RC-4B/C rat pituitary cells $^{125}$I-rat PrRP31 K_i (Nm) | % of PrRP31 | GPR10 human receptor transfected in CHO cells K_i (Nm) | % of PrRP31 | Food intake in mice (5 mg/kg) % of saline-treated group |
|---|---|---|---|---|---|---|---|
| 49 | 9 | (N-stear)SRAHQHS Nle ETRTPDI NPAWYTGRGIRPVGRF-NH$_2$ | 0.96 ± 0.10 | 514 | 5.39 ± 0.58 | 7 | 3.5 |
| 50 | 10 | SRAHQHSNleETRTPDI NPAWYTGRGIRPVGR 1-Nal-NH$_2$ | 102 ± 19.1 | 4.8 | 34.52 ± 16.00 | 11 | NT |
| 51 | 11 | (N-myr)SRAHQHS Nle ETRTPDI NPAWYTGRGIRPVGR 1-Nal-NH$_2$ | 3.96 ± 1.22 | 124 | 1.33 ± 0.22 | 292 | NT |
| 52 | 12 | (N-palm)SRAHQHS Nle ETRTPDI NPAWYTGRGIRPVGR 1-Nal-NH$_2$ | 2.17 ± 1.29 | 111 | 4.27 ± 0.77 | 91 | 13 |
| 53 | 13 | SRAHQHS Nle ETRTPDI NPAWYTGRGIRPVGR PheCl$_2$—NH$_2$ | 3.84 ± 0.93 | 128 | 2.27 ± 0.48 | 171 | NT |
| 54 | 14 | (N-myr)SRAHQHS Nle ETRTPDI NPAWYTGRGIRPVGR PheCl$_2$—NH$_2$ | 1.79 ± 1.02 | 275 | 0.95 ± 0.33 | 409 | 13 |
| 55 | 15 | (N-palm)SRAHQHS Nle ETRTPDI NPAWYTGRGIRPVGR PheCl$_2$—NH$_2$ | 1.30 ± 0.29 | 379 | 1.05 ± 0.41 | 370 | 5 |
| 56 | 16 | SRAHQHS Nle ETRTPDI NPAWYTGRGIRPVGR PheNO$_2$—NH$_2$ | 19.90 ± 5.9 | 2.5 | 4.80 ± 0.88 | 81 | NT |
| 57 | 17 | (N-myr)SRAHQHS Nle ETRTPDI NPAWYTGRGIRPVGR PheNO$_2$—NH$_2$ | 1.97 ± 1.26 | 250 | 1.59 ± 1.05 | 245 | NT |
| 58 | 18 | (N-palm)SRAHQHS Nle ETRTRDI NPAWYTGRGIRPVGR PheNO$_2$—NH$_2$ | 0.58 ± 0.10 | 850 | 0.77 ± 0.28 | 505 | 0.7 |
| 59 | 19 scram | SHQRPADTHWYPRG Nle FPTIGRITARNGEVSR | 1317000 ± 1259000 | 0.00004 | >10$^7$ | | NT |
| 60 | 20 scram | (N-myr)SHQRPADTHWYPRG Nle FPTIGRITARNGEVSR | 123 ± 16.1 | 4.6 | 262.0 ± 55.4 | 1.5 | 100 |
| 61 | 21 | SRAHQHS Nle ETRTPDI NPAWYTGRGIRPVGR PheF$_5$—NH$_2$ | 9.69 ± 1.86 | 51 | 8.59 ± 1.20 | 45 | NT |
| 62 | 22 | (N-palm)SRAHQHS Nle ETRTPDI NPAWYTGRGIRPVGR PheF$_5$—NH$_2$ | 0.51 ± 0.08 | 966 | 1.92 ± 0.53 | 203 | 41 |
| 63 | 23 | SRAHQHS Nle ETRTPDI NPAWYTGRGIRPVGR Tyr-NH$_2$ | 3.25 ± 0.15 | 152 | 2.02 ± 0.09 | 193 | NT |
| 64 | 24 | (N-palm)SRAHQHS Nle ETRTPDI NPAWYTGRGIRPVGR Tyr-NH$_2$ | 0.44 ± 0.22 | 1120 | 1.57 ± 0.39 | 248 | 22 |

TABLE 2-continued

Affinity to the rat receptor in RC-4B/C cells and human GPR10 receptor transfected in CHO cells, and food intake in fasted mice (45 min after SC injection).

| SEQ ID NO | Analog no. | Sequence | RC-4B/C rat pituitary cells $^{125}$I-rat PrRP31 $K_i$ (Nm) | % of PrRP31 | GPR10 human receptor transfected in CHO cells $K_i$ (Nm) | % of PrRP31 | Food intake in mice (5 mg/kg) % of saline-treated group |
|---|---|---|---|---|---|---|---|
| 65 | 25 scram | D-Phe-D-Arg-GVPRIGRGTYWAPNIDPT-NH$_2$ | 5200 ± 420 | 0.09 | 6290 ± 3970 | 0.06 | NT |
| 66 | 26 scram | (N-myr)D-Phe-D-Arg-GVPRIGRGTYWAPNIDPT-NH$_2$ | 364 ± 83 | 1.4 | >10$^7$ | | 100 |
| 67 | 27 | TPDINPAWYTGR Sar IRPVGRF-NH$_2$ | 7.94 ± 3.74 | 62 | 4.51 ± 1.49 | 86 | NT |
| 68 | 28 | (N-myr)TPDINPAWYTGR Sar IRPVGRF-NH$_2$ | 0.32 ± 0.07 | 1541 | 3.12 ± 0.37 | 125 | NT |
| 69 | 29 | TPDINPAWY N-Me-Ala SRGIRPVGRF-NH$_2$ | 49.4 ± 9.35 | 10 | 8.72 ± 2.22 | 45 | NT |
| 70 | 30 | (N-myr)TPDINPAWY N-Me-Ala SRGIRPVGRF-NH$_2$ | 0.46 ± 0.05 | 1072 | 2.10 ± 0.77 | 185 | NT |
| 71 | 31 | TPDINPAWYTGRGARPFGRF-NH$_2$ | 655 ± 164 | 0.8 | 583 ± 293 | 0.7 | NT |
| 72 | 32 | (N-myr)TPDINPAWYTGRGARPFGRF-NH$_2$ | 7.21 ± 0.71 | 68 | 8.47 ± 3.18 | 46 | NT |
| 73 | 33 | TPDINPAWYASRPFRPVGRF-NH$_2$ | 2.14 ± 0.53 | 230 | 1.73 ± 0.22 | 225 | NT |
| 74 | 34 | (N-myr)TPDINPAWYASRPFRPVGRF-NH$_2$ | 0.84 ± 0.17 | 587 | 0.58 ± 0.26 | 671 | NT |
| 75 | 35 short. | Nle-ETRTPDINPAWYTGRGIRPVGRF-NH$_2$ | 2.94 ± 0.62 | 168 | 3.44 ± 0.48 | 113 | NT |
| 76 | 36 short. | (N-myr)Nle-ETRTPDINPAWYTGRGIRPVGRF-NH$_2$ | 0.45 ± 0.04 | 1096 | 5.48 ± 0.64 | 71 | NT |
| 77 | 37 short. | QHSMETRTPDINPAWYTGRGIRPVGRF-NH$_2$ | 2.61 ± 0.15 | 189 | 5.92 ± 0.76 | 66 | NT |
| 78 | 38 short. | (N-myr)QHSMETRTPDINPAWYTGRGIRPVGRF-NH$_2$ | 0.37 ± 0.11 | 1332 | 6.93 ± 4.74 | 56 | NT |
| 79 | 39 | (N-oct)TPDINPAWYASRGIRPVGRF-NH$_2$ | 0.93 ± 0.23 | 530 | 1.94 ± 0.32 | 201 | 100 |
| 80 | 40 | (N-dec)TPDINPAWYASRGIRPVGRF-NH$_2$ | 0.41 ± 0.01 | 1202 | 3.02 ± 0.49 | 129 | 100 |
| 81 | 41 | (N-dodec)TPDINPAWYASRGIRPVGRF-NH$_2$ | 0.60 ± 0.22 | 822 | 2.41 ± 0.26 | 161 | 85 |
| 82 | 42 | (N-myr)SRTHRHSMEIRTPDINPAWYASRGI RPVGRF-NH$_2$ | 0.48 ± 0.18 | 1027 | 4.70 ± 0.25 | 83 | 10 |
| 83 | 43 | (N-palm)SRTHRHSMEIRTPDINPAWYASRGIRPVGRF-NH$_2$ | 0.95 ± 0.35 | 519 | 4.32 ± 0.43 | 90 | 30 |

TABLE 2-continued

Affinity to the rat receptor in RC-4B/C cells and human GPR10 receptor transfected in CHO cells, and food intake in fasted mice (45 min after SC injection).

| SEQ ID NO | Analog no. | Sequence | RC-4B/C rat pituitary cells $^{125}$I-rat PrRP31 | | GPR10 human receptor transfected in CHO cells | | Food intake in mice (5 mg/kg) % of saline-treated group |
|---|---|---|---|---|---|---|---|
| | | | $K_i$ (Nm) | % of PrRP31 | $K_i$ (Nm) | % of PrRP31 | |
| 84 | 44 | (N-palm)SRTHRHSMEIRTPDIN PAWYASRGIRPVGRF-NHMe | NT | | 3.16 ± 0.51 | 123 | NT |
| 85 | 45 | (N-palm)SRTHRHSMEIRTPDIN PAWYASRGIRPVGRF-NOMe | NT | | 4.21 ± 0.55 | 92 | NT |
| 86 | 46 | (N-myr)SRAHQHSMETRTPDIN PAWYTGRGIRPVGRF-NH$_2$ | 0.75 ± 0.10 | 657 | NT | | 20 |
| 87 | 47 | (N-palm)SRAHQHSMETRTPDIN PAWYTGRGIRPVGRF-NH$_2$ | 0.41 ± 0.12 | 1202 | NT | | 2 |
| 88 | 48 | SRTHRHSMEIK(N-palm)TPDIN PAWYASRGIRPVGRF-NH$_2$ | NT | | 6.37 ± 0.78 | 61 | 13 |
| 89 | 49 | TPDIK(N-palm)PAWYASRGIR PVGRF-NH$_2$ | NT | | 4.34 ± 0.45 | 90 | NT |
| 90 | 50 | TPDINPK(N-palm)WYASRGIR PVGRF-NH$_2$ | NT | | 5.64 ± 0.35 | 69 | NT |
| 91 | 51 | SRTHRHSMEIRTPDINPK(N-palm) WYASRGIRPVGRF-NH$_2$ | NT | | 7.24 ± 0.13 | 54 | 20 |
| 92 | 52 | SRTHRHSMEIK(N-Γe(N-palm)) TPDINPAWYASRGIRPVGR F-NH$_2$ | 4.23 ± 2.11 | 57 | 5.95 ± 0.72 | 65 | 10 |
| 93 | 53 | SRTHRHSMEIK(N-GABA(N-palm)) TPDINPAWYASRGIRPVGR F-NH$_2$ | 1.26 ± 0.57 | 190 | 9.19 ± 0.96 | 42.5 | 25 |
| 94 | 54 | (N-palm)γ-ESRTHRHSMEIR TPDINPAWYASRGIRPVGR F-NH$_2$ | 0.50 ± 0.13 | 119 | 6.90 ± 1.0 | 57 | 14 |
| 95 | 55 | SETHRHSMEIK(N-Γe(N-palm)) TPDINPAWYASRGIRPVGR F-NH$_2$ | X.35 ± 0.67 | 236 | 4.72 ± 0.35 | 83 | 12 |
| 96 | 56 | SETHEHSMEIK(N-Γe(N-palm)) TPDINPAWYASRGIRPVGR F-NH$_2$ | 4.23 ± 2.11 | 57 | 5.66 ± 0.39 | 57 | 10 |
| 97 | 57 | SRTHRHSMEIK(N-palm(N-POE)) TPDINPAWYASRGIRPVGR F-NH$_2$ | 0.36 ± 0.16 | 663 | 3.79 ± 0.46 | 103 | 10 |
| 98 | 58 | SETHRHSMEIK(N-POE(N-palm)) TPDINPAWYASRGIRPVGR F-NH$_2$ | 0.41 ± 0.28 | 575 | 3.79 ± 0.58 | 103 | 7 |

TABLE 2-continued

Affinity to the rat receptor in RC-4B/C cells and human GPR10 receptor transfected in CHO cells, and food intake in fasted mice (45 min after SC injection).

| SEQ ID NO | Analog no. | Sequence | RC-4B/C rat pituitary cells $^{25}$I-rat PrRP31 $K_i$ (Nm) | % of PrRP31 | GPR10 human receptor transfected in CHO cells $K_i$ (Nm) | % of PrRP31 | Food intake in mice (5 mg/kg) % of saline-treated group |
|---|---|---|---|---|---|---|---|
| 99 | 59 | (N-palm(N-POE))SRTHRHS MEIK (N-palm(N-POE))TPDINPAWYASR GIRPVGRF-NH$_2$ | 2.82 ± 0.94 | 85 | 32.4 ± 3.57 | 12 | 23 |

TABLE 3

Cumulative food intake after repeated administration of vehicle and compounds 43 and 52 (IP, doses 1 and 5 mg/kg) to ZDF diabetic rats (n = 8). *P < 0.05, P < 0.01, *P < 0.001 vs control group.

| | Food intake (g) | | | |
|---|---|---|---|---|
| Analog/dose | Day 1 | Day 1-7 | Day 1-14 | Day 1-21 |
| Control | 48.8 ± 2.4 | 349.6 ± 16.4 | 655.0 ± 25.7 | 896.7 ± 39.0 |
| 43 1 mg/kg | 40.8 ± 2.1 | 299.9 ± 8.9 | 572.5 ± 15.5 | 817.7 ± 22.1 |
| 43 5 mg/kg | 34.2 ± 3.5*** | 273.3 ± 20.4** | 528.9 ± 36.0** | 768.2 ± 49.8* |
| 52 1 mg/kg | 43.0 ± 2.2 | 306.9 ± 11.8 | 570.9 ± 17.1 | 811.5 ± 23.6 |
| 52 5 mg/kg | 42.4 ± 2.1 | 287.8 ± 12.5* | 559.0 ± 21.0* | 814.8 ± 26.1 |

TABLE 4

Metabolic parameters after repeated administration of vehicle and compounds 43 and 52 (IP, doses 1 and 5 mg/kg) to ZDF diabetic rats on day 21 (end of experiment) (n = 8). *P < 0.05, **P < 0.01 vs control group.

| Analog/dose | Cholesterol (mmol/l) | Leptin (pg/ml) | Insulin (pmol/l) |
|---|---|---|---|
| Control | 3.79 ± 0.30 | 16584 ± 1380 | 265.31 ± 48.96 |
| 43 1 mg/kg | 3.10 ± 0.12* | 13297 ± 921 | 267.69 ± 40.69 |
| 43 5 mg/kg | 2.91 ± 0.12** | 16560 ± 4843 | 271.84 ± 34.00 |
| 52 1 mg/kg | 3.71 ± 0.16 | 16336 ± 1466 | 268.94 ± 43.40 |
| 52 5 mg/kg | 3.19 ± 0.16 | 11372 ± 427 | 183.35 ± 37.49 |

While specific embodiments described herein have been shown and described in detail to illustrate the application of the principles of the lipidated analog of prolactin releasing peptide (PrRP)s described herein, it will be understood that the lipidated analog of prolactin releasing peptide (PrRP)s may be embodied otherwise without departing from such principles. Numerous variations, changes, and substitutions will be understood by those skilled in the art without departing from the lipidated analog of prolactin releasing peptide (PrRP)s described herein. It should be understood that various alternatives to the specific embodiments of the lipidated analog of prolactin releasing peptide (PrRP)s described herein may be employed in practicing the invention. It is intended that the claims define the scope of the invention, and that methods and structures within the scope of these claims and their equivalents be covered thereby.

The invention claimed is:

1. A method of lowering blood glucose, the method comprising administering a lipidated analog of prolactin releasing peptide (PrRP) to a subject, wherein the lipidated analog of prolactin releasing peptide (PrRP) is selected from the group consisting of:

SRTHRHSMEIKTPDINPAWYASRGIRPVGRF-NH$_2$; and
$\quad\quad\quad\quad\quad\quad$|
$\quad\quad\quad\quad\quad\quad$X$^2$(palm)
(SEQ ID NO: 14)

TPDINPKWYASRGIRPVGRF-NH$_2$;
$\quad$|
$\quad$X$^2$(palm)
(SEQ ID NO: 15)

wherein palm is palmitic acid, and wherein X$^2$ is γ-glutamic acid.

2. The method of claim 1, wherein the lipidated analog of prolactin releasing peptide (PrRP) is administered to the subject as part of a pharmaceutical formulation.

* * * * *